US012742194B2

(12) United States Patent
Brown

(10) Patent No.: US 12,742,194 B2
(45) Date of Patent: Sep. 22, 2026

(54) METHODS AND COMPOSITIONS FOR HIGH THROUGHPUT SAMPLE PREPARATION USING DOUBLE UNIQUE DUAL INDEXING

(71) Applicant: Twist Bioscience Corporation, South San Francisco, CA (US)

(72) Inventor: Keith Brown, Carlsbad, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 1191 days.

(21) Appl. No.: 17/628,861

(22) PCT Filed: Jul. 22, 2020

(86) PCT No.: PCT/US2020/043146
§ 371 (c)(1),
(2) Date: Jan. 20, 2022

(87) PCT Pub. No.: WO2021/016395
PCT Pub. Date: Jan. 28, 2021

(65) Prior Publication Data

US 2022/0259638 A1 Aug. 18, 2022

Related U.S. Application Data

(60) Provisional application No. 62/901,958, filed on Sep. 18, 2019, provisional application No. 62/877,197, filed on Jul. 22, 2019.

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01)

(58) Field of Classification Search
None
See application file for complete search history.

(56) References Cited

U.S. PATENT DOCUMENTS 4,318,846 A 3/1982 Khanna et al.
4,437,975 A 3/1984 Gillespie et al.
4,683,195 A 7/1987 Mullis et al.
4,683,202 A 7/1987 Mullis
4,757,141 A 7/1988 Fung et al.
4,988,617 A 1/1991 Landegren et al.
5,066,580 A 11/1991 Lee
5,091,519 A 2/1992 Cruickshank
5,151,507 A 9/1992 Hobbs, Jr. et al.
5,188,934 A 2/1993 Menchen et al.
5,242,794 A 9/1993 Whiteley et al.
5,270,184 A 12/1993 Walker et al.
5,366,860 A 11/1994 Bergot et al.
5,399,491 A 3/1995 Kacian et al.
5,405,746 A 4/1995 Uhlen
5,409,818 A 4/1995 Davey et al.
5,413,909 A 5/1995 Bassam et al.
5,422,252 A 6/1995 Walker et al.
5,494,810 A 2/1996 Barany et al.
5,500,356 A 3/1996 Li et al.
5,554,517 A 9/1996 Davey et al.
5,648,245 A 7/1997 Fire et al.
5,688,648 A 11/1997 Mathies et al.
5,759,778 A 6/1998 Li et al.
5,800,996 A 9/1998 Lee et al.
5,847,162 A 12/1998 Lee et al.
5,861,245 A 1/1999 Mcclelland et al.
5,990,479 A 11/1999 Weiss et al.
6,027,923 A 2/2000 Wallace
6,063,603 A 5/2000 Davey et al.
6,207,392 B1 3/2001 Weiss et al.
6,210,891 B1 4/2001 Nyren et al.
6,251,303 B1 6/2001 Bawendi et al.
6,309,824 B1 10/2001 Drmanac
6,319,426 B1 11/2001 Bawendi et al.
6,322,901 B1 11/2001 Bawendi et al.
6,401,267 B1 6/2002 Drmanac
6,410,276 B1 6/2002 Burg et al.
6,423,551 B1 7/2002 Weiss et al.
6,426,513 B1 7/2002 Bawendi et al.
6,444,143 B2 9/2002 Bawendi et al.
6,576,291 B2 6/2003 Bawendi et al.
6,582,938 B1 6/2003 Su et al.
6,828,100 B1 12/2004 Ronaghi
6,833,246 B2 12/2004 Balasubramanian
6,864,052 B1 3/2005 Drmanac et al.
6,911,345 B2 6/2005 Quake et al.
7,232,656 B2 6/2007 Balasubramanian et al.
(Continued)

FOREIGN PATENT DOCUMENTS

CN 102439177 A 5/2012
WO WO-8706270 A1 10/1987
(Continued)

OTHER PUBLICATIONS

Halldorsson et al.: Science. 363(6425)eaau1043 (2019).
Mackiewicz et al.: Distribution of Recombination Hotspots in the Human Genome—A Comparison of Computer Simulations with Real Data. PLOS ONE. 8(6):e65272 (2013).
PCT/US2020/043146 International Preliminary Report on Patentability dated Feb. 3, 2022.
PCT/US2020/043146 International Search Report and Written Opinion dated Dec. 18, 2020.
Ciprianay, B. et al. Real-Time Analysis and Selection of Methylated DNA by Flourescence-Activated Single Molecule Sorting in a Nanofluidic Channel. Proceedings of the National Acadamy of Sciences. May 29, 2012 (published online before print May 14, 2012), vol. 109, No. 22, pp. 8477-8482.
(Continued)

*Primary Examiner* — Juliet C Switzer
*Assistant Examiner* — Brian Ellis Young
(74) *Attorney, Agent, or Firm* — Bookoff McAndrews, PLLC

(57) ABSTRACT

Provided herein are methods and compositions for high throughput sample preparation using double unique dual indexing.

20 Claims, 37 Drawing Sheets

(56) References Cited

U.S. PATENT DOCUMENTS

| | | | | |
|---|---|---|---|---|
| 7,459,311 | B2 | 12/2008 | Nyren et al. | |
| 7,648,824 | B2 | 1/2010 | Nyren et al. | |
| 7,670,810 | B2 | 3/2010 | Gunderson et al. | |
| 8,114,978 | B2 | 2/2012 | Jones et al. | |
| 8,168,385 | B2 | 5/2012 | Brenner | |
| 8,722,326 | B2 | 5/2014 | Drmanac et al. | |
| 9,968,901 | B2 | 5/2018 | Head et al. | |
| 10,450,562 | B2 | 10/2019 | Brown | |
| 10,780,412 | B2 | 9/2020 | Head et al. | |
| 11,214,798 | B2 | 1/2022 | Brown | |
| 11,752,483 | B2 | 9/2023 | Head et al. | |
| 2002/0045045 | A1 | 4/2002 | Adams et al. | |
| 2003/0017264 | A1 | 1/2003 | Treadway et al. | |
| 2003/0143599 | A1 | 7/2003 | Makarov et al. | |
| 2005/0191656 | A1 | 9/2005 | Drmanac et al. | |
| 2006/0252060 | A1 | 11/2006 | Willis et al. | |
| 2007/0207482 | A1 | 9/2007 | Church et al. | |
| 2007/0264642 | A1 | 11/2007 | Willis et al. | |
| 2009/0018024 | A1 | 1/2009 | Church et al. | |
| 2009/0036325 | A1 | 2/2009 | Mckernan et al. | |
| 2009/0118128 | A1 | 5/2009 | Liu et al. | |
| 2010/0105052 | A1 | 4/2010 | Drmanac et al. | |
| 2010/0222238 | A1 | 9/2010 | Smith et al. | |
| 2010/0273219 | A1 | 10/2010 | May et al. | |
| 2010/0311064 | A1 | 12/2010 | Oliphant et al. | |
| 2015/0329855 | A1* | 11/2015 | Gray | C12Q 1/6855 506/26 |
| 2016/0053253 | A1* | 2/2016 | Salathia | C12N 15/1093 506/4 |
| 2017/0022551 | A1* | 1/2017 | Liu | C12Q 1/6848 |
| 2017/0247689 | A1* | 8/2017 | Brown | C12N 15/1093 |
| 2021/0121845 | A1 | 4/2021 | Head et al. | |
| 2022/0073909 | A1 | 3/2022 | Brown | |

FOREIGN PATENT DOCUMENTS

| | | | |
|---|---|---|---|
| WO | WO-9006995 | A1 | 6/1990 |
| WO | WO-2006137733 | A1 | 12/2006 |
| WO | WO-2007073171 | A2 | 6/2007 |
| WO | WO-2011142836 | A9 | 1/2012 |
| WO | 2012112804 | A1 | 8/2012 |
| WO | WO-2013010062 | A2 | 1/2013 |
| WO | 2013096802 | A1 | 6/2013 |
| WO | WO-2013177220 | A1 | 11/2013 |
| WO | WO-2016040524 | A1 | 3/2016 |
| WO | 2018236918 | A1 | 12/2018 |
| WO | WO-2021016395 | A1 | 1/2021 |

OTHER PUBLICATIONS

Drmanac et al. Human genome sequencing using unchained base reads on self-assembling DNA nanoarrays. Science. 327: 78-81 (2010).

Grillo et al., Cleanup: a fast computer program for removing redundancies from nucleotide sequence databases. Bioinformatics. 12(1): 1—(1996).

Guatelli et al. Isothermal, in vitro amplification of nucleic acids by a multienzyme reaction modeled after retroviral replication. PNAS USA 87(5):1874-1878 (1990).

Hamady, M. et al. Error-Correcting Barcoded Primer for Pyrosequencing Hundreds of Samples in Multiplex. Nat. Methods. 5(3): 235-237 (2008).

Jeppe et al., Discarding duplicate ditags inLongSAGE analysis may introduce significant error. Bmc Bioinformatics. 8:92 (2007).12 pages.

Kienzler, R. et al. Large-Scale DNA Sequence Analysis in the Cloud: A Stream-Based Approach. Euro-Par 20122: Parallel Processing Workshops Lecture Notes in Computer Science. 7156: 467-476 (2012).

Kim et al. Digital genotyping using molecular affinity and mass spectrometry. Nat Rev Gene 4(12):1001-1008 (2003).

Kim S. et al. Solid phase capturable dideoxynucleotides for multiplex genotyping using mass spectrometry. Nucleic Acids Research 30(16); e85 (2002).

Landegren et al., A ligase-mediated gene detection technique. Science 241(4869): 1077-1080 (1988).

Li et al. A photocleavable fluorescent nucleotide for DNA sequencing and analysis. PNAS USA 100:414-419 (2003).

Makrigiorgos, et al., A PCR-Based amplificationmethod retaining quantitative difference between two complex genomes. NatureBiotech 20(9): 936-939 (2002).

Meyer, M. et al. Targeted High-Throughput Sequencing of Tagged Nucleic Acid Samples. Nucleic Acids Research. 35(15): e97 (2007). 5 pages.

Nunez et al. Application of Circular Ligase to Provide Template for Rolling Circle Amplification of Low Amounts of Fragmented DNA. FBI Publication (2008).

Orsouw, Nathalie J. et al. Complexity Reduction of Polymorphic Sequences (CRoPS): A Novel Approach for Large-Scale Polymorphism Discovery in Complex Genomes. PLoS One, 2(11): e1172 (2007). 10 pages.

PCT/US2013/042106 International Preliminary Report on Patentability Dated Nov. 25, 2014.

PCT/US2013/042106 International Search Report and Written Opinion Dated Oct. 17, 2013.

PCT/US2015/049249 International Search Report and Written Opinion Mailed Feb. 3, 2016.

Qiu, Chunmei et al. Design and synthesis of cleavable biotinylated dideoxynucleotides for DNA sequencing by matrix-assisted laser desorption/ionization time-of-flight mass spectrometry. Analytical Biochemistry. 427(2): 193-201 (2012).

Quan et al. Parallel on-chip gene synthesis and application to optimization of protein expression. Nat. Biotechnol. 29:449-452 (2011), E-published Apr. 24, 2011.

Qui et al., Analytical Biochemistry, vol. 427, No. 2, pp. 193-201, Apr. 25, 2012.

Tong, AK., et al. Single nucleotide polymorphism detection by combinatorial fluorescence energy transfer tags and biotinylated dideoxynucleotides. Nucleic Acids Research 30(5); e19 (2002).

U.S. Appl. No. 14/549,411 Non-Final Office Action Mailed Jun. 13, 2017.

U.S. Appl. No. 16/563,233 Non-Final Office Action dated Jan. 14, 2021.

U.S. Appl. No. 15/948,459 Office Action dated Nov. 25, 2019.

U.S. Appl. No. 15/509,747 Office Action dated Jan. 10, 2019.

Van Dijk, Erwin L., et al. Library preparation methods for next-generation sequencing: tone down the bias. Experimental Cell Research, 322(1): 12-20 (2014).

Wachter A., et al. A 50 SNP-multiplex mass spectrometry assay for human identification. Forensic Science International: Genetics Supplemental Series, 1(1): 487-489 (2008).

Walker et al., SEALS: a system for easy analysis of lots of sequences. International Conference on Intelligent Systems for Molecular. XP055295893 (1997). 8 pages.

Walker et al., Strand displacement amplification-an isothermal, in vitro DNA amplification technique. Nucleic Acids Res. 20(7):1691-6 (1992).

Wetmur, James G., DNA Probes: Applications of the Principles of Nucleic Acid Hybridization. Critical Reviews in Biochemistry and Molecular Biology 26(3/4): 227-259 (1991).

Wilhelm, B. et al. RNA-Seq-quantitative measurement of expression through massively parallel RNA-sequencing. Methods 48(3): 249-257 (2009).

Wu & Wallace, The ligation amplification reaction (LAR)—Amplification of specific DNA sequences using sequential rounds of template-dependent ligation. (Ligase Chain Reaction (LR)) Genomics 4(4): 560-569 (1989).

* cited by examiner

P=Plate barcode
a,b= Forward, Reverse orientation
S = Sample barcode
N=barcode number (i.e. 1-96)

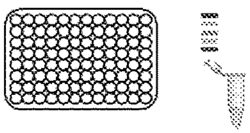
Double barcoded products from a plate are pooled into a single tube.
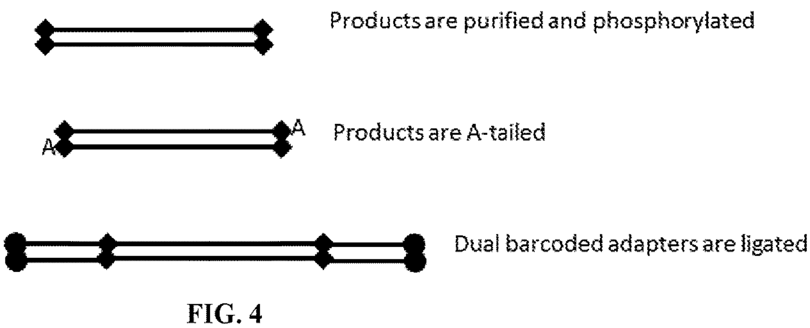
FIG. 4
Pre-amplification of targeted loci?
Multiplex PCR w/ >1kb products per target locus. Primers are universal and generated via microarray synthesis. Amplification may occur simultaneously or in serial.
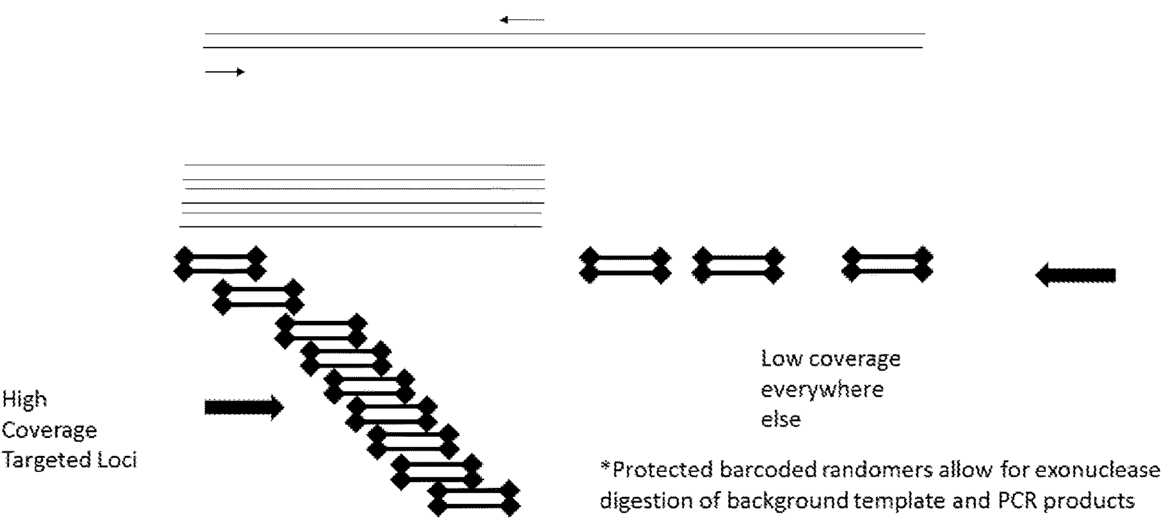
FIG. 5

| group | Alignment Summary M | Alignment Summ | Alignment Sum | Alignment S | Alignment Sum | Alignment Summa | Duplication Metrics | Duplication Me | Gc Bias Sum | Gc Bias Summ | Insert Size M | Whole Genome C | Whole Genome | Whole Genome Coverage M |
|---|---|---|---|---|---|---|---|---|---|---|---|---|---|---|
| category | PAIR | PAIR | PAIR | PAIR | PAIR | PAIR | NONE | NONE | NONE | NONE | FR | WHOLE_GENOM | NON_ZERO_RE | WHOLE_GENOME |
| name | Fraction Paired Reads | Mismatch Rate | HQError Rate | Indel Rate | %Reads Aligne | % Chimeras(>10Kb | Duplication Rate(P | Estimated Libr | AT Dropout | GC Dropout | Median Inser | Mean Coverage | Mean Non-Zero | % Coverage at 1x |
| DOL1_S1. | 0.986416 | 0.008744 | 0.007195 | 0.000425 | 0.993287 | 0.046593 | 0.309166 | 1254305 | 2.724911 | 5.658508 | 292 | 0.019213 | 1.127643 | 0.017038 |
| DOL1_S2. | 0.98039 | 0.010183 | 0.009398 | 0.000297 | 0.987918 | 0.040138 | 0.271216 | 1470593 | 2.565963 | 3.639247 | 302 | 0.020033 | 1.073493 | 0.018661 |
| DOL1_S3. | 0.984386 | 0.007892 | 0.006776 | 0.000313 | 0.991855 | 0.052543 | 0.368027 | 580344 | 1.952999 | 6.06379 | 299 | 0.009915 | 1.071796 | 0.009251 |
| NEB1_S4. | 0.989037 | 0.009041 | 0.007798 | 0.000199 | 0.995927 | 0.001534 | 0.108105 | 4251513 | 1.340995 | 1.449665 | 330 | 0.040124 | 1.038748 | 0.038627 |
| NEB2_S5. | 0.989075 | 0.009203 | 0.007956 | 0.000198 | 0.995733 | 0.001733 | 0.09466 | 4902414 | 1.300517 | 1.640627 | 329 | 0.040746 | 1.038821 | 0.039223 |
| Rip1_S1.d | 0.982183 | 0.012655 | 0.011631 | 0.000603 | 0.988871 | 0.017694 | 0.102756 | 4441288 | 4.604247 | 2.462883 | 333 | 0.034578 | 1.083392 | 0.031916 |
| Rip2_S2.d | 0.980135 | 0.012151 | 0.011097 | 0.000608 | 0.987091 | 0.030655 | 0.121064 | 3710174 | 4.595586 | 2.376328 | 331 | 0.033604 | 1.08301 | 0.031029 |
| ZOM1_S6. | 0.955232 | 0.007051 | 0.006155 | 0.00036 | 0.990089 | 0.051842 | 0.369648 | 794854 | 7.060051 | 14.931347 | 312 | 0.01692 | 1.054627 | 0.016043 |
| ZOM2_S7. | 0.911587 | 0.009378 | 0.007715 | 0.00042 | 0.98996 | 0.051512 | 0.255148 | 1542572 | 1.910888 | 9.163981 | 276 | 0.0222 | 1.087215 | 0.020419 |
| ZOM3_S8. | 0.912399 | 0.009367 | 0.004753 | 0.000459 | 0.990368 | 0.051964 | 0.292464 | 1300244 | 3.346138 | 7.032795 | 266 | 0.020551 | 1.108058 | 0.018547 |

FIG. 6

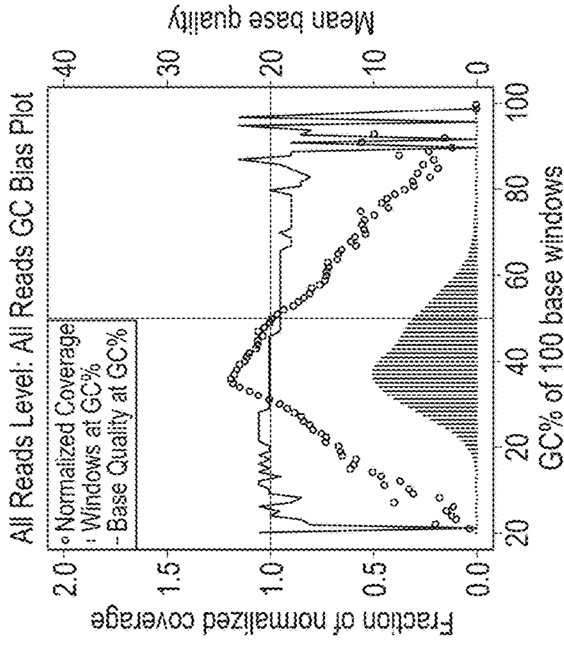
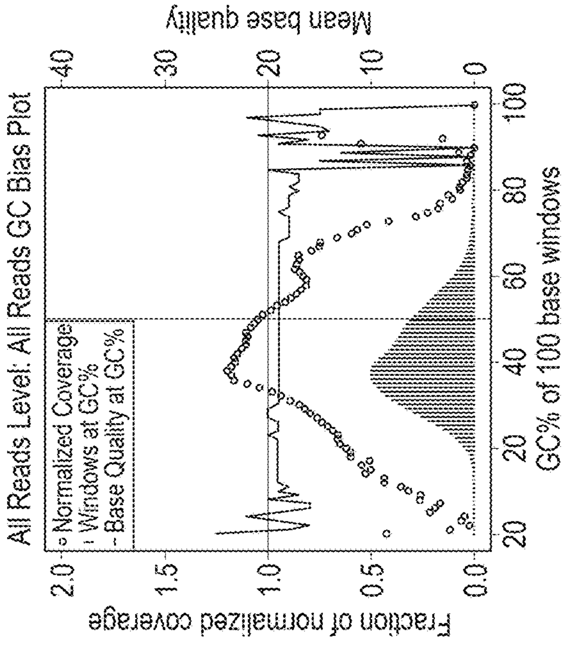
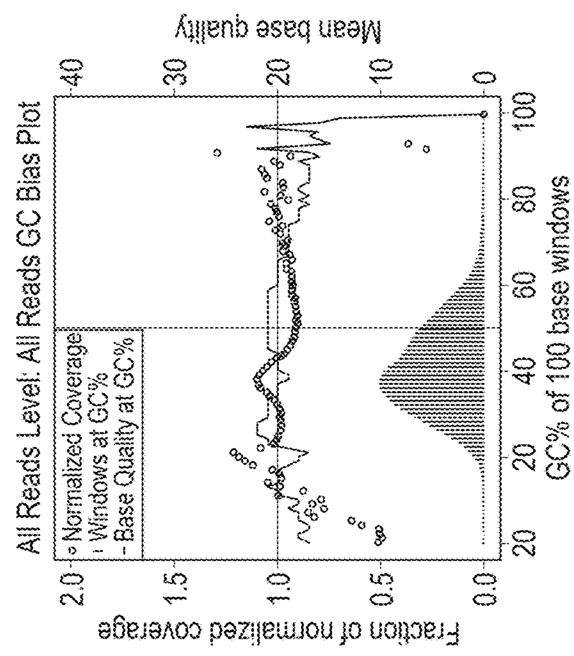
FIG. 7

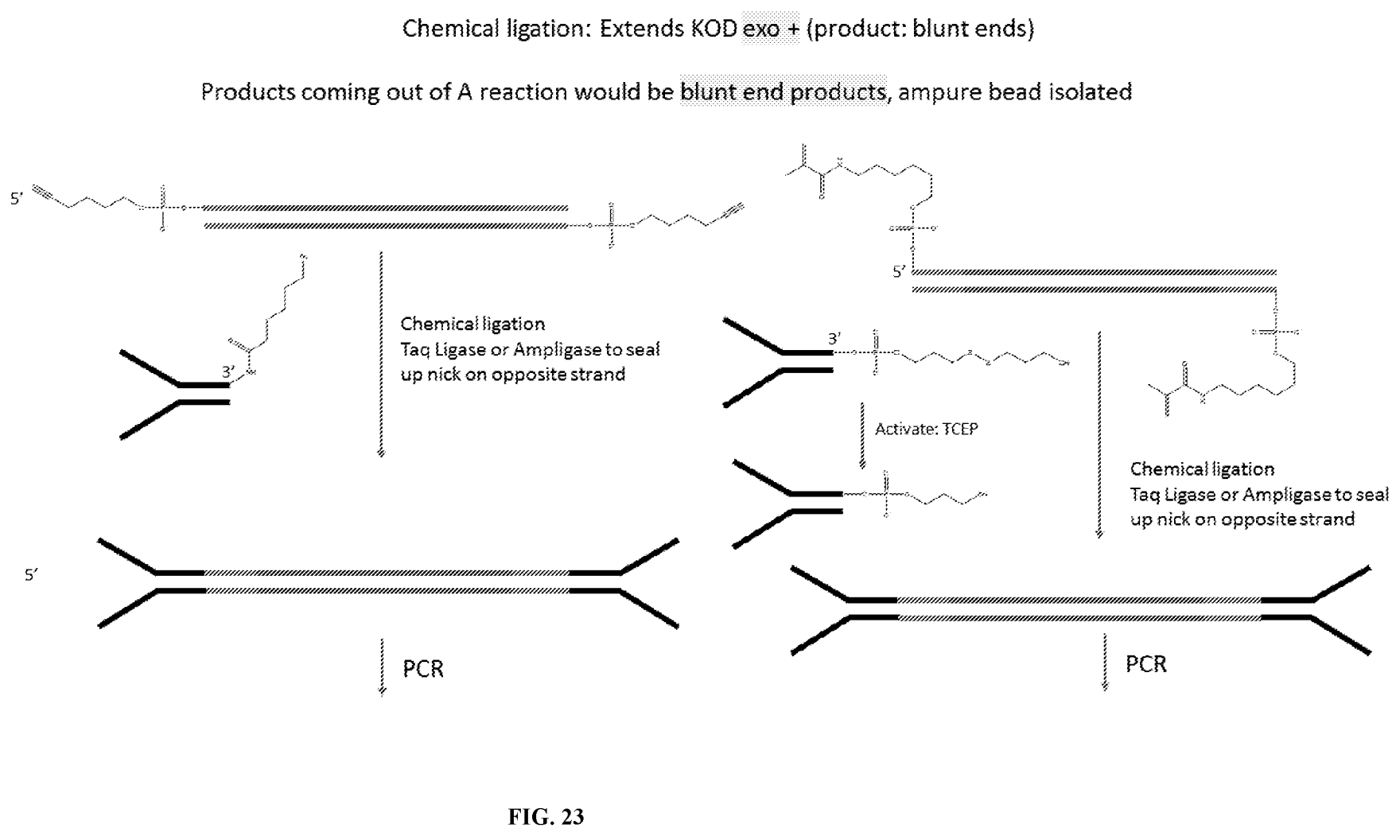

Chemical ligation: Extends KOD exo + (product: blunt ends)

Products coming out of A reaction would be blunt end products, ampure bead isolated

5'

3'

Chemical ligation
Taq Ligase or Ampligase to seal up nick on opposite strand

5'

PCR

5'

3'

Activate: TCEP

Chemical ligation
Taq Ligase or Ampligase to seal up nick on opposite strand

PCR

FIG. 23

Template switching method

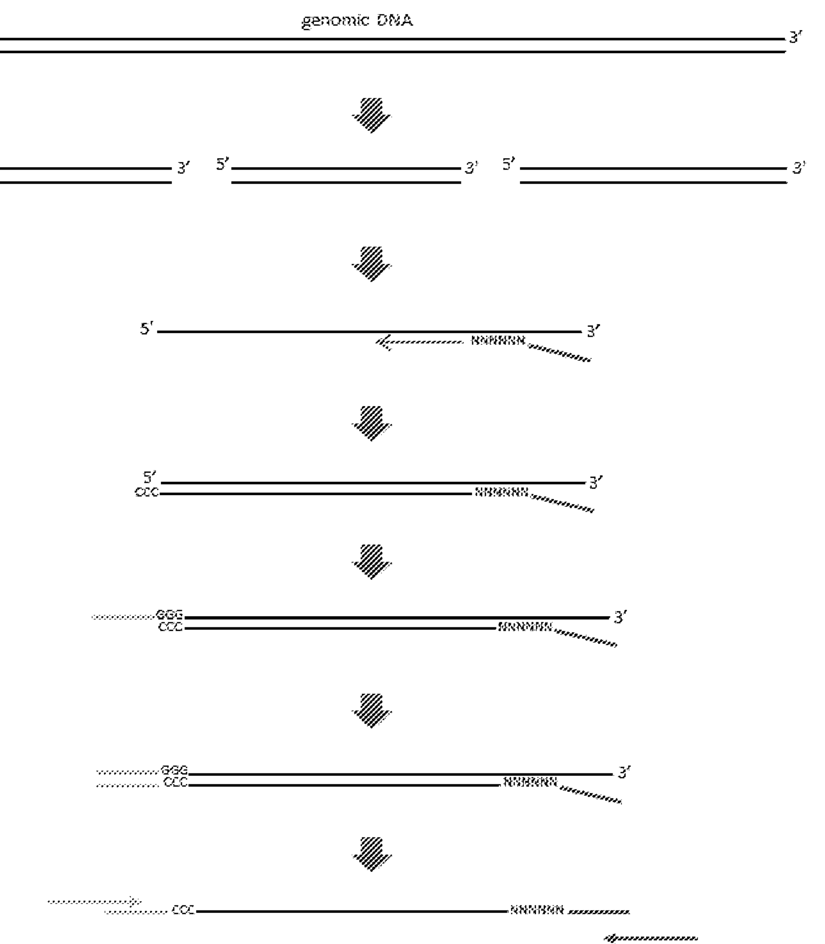

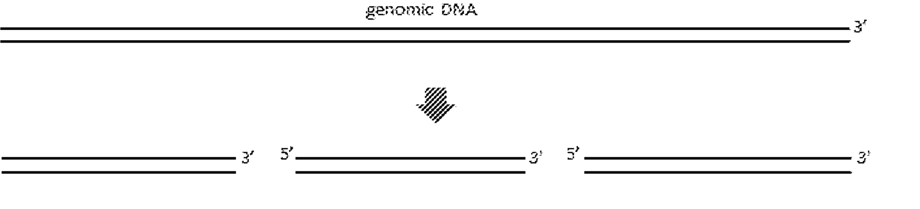

- Ninety-six or greater DNA samples.
- Fragment each DNA sample (enzymatically or by shearing)
- Heat denature DNA.
- Random prime with reverse transcriptase, such as MMLV.
- MMLV can use RNA or ssDNA as template
- Random primer carries barcode unique to each sample and partial Illumina adapter.
- MMLV adds non-templated C nucleotides at the end.
- Oligo with GGG overhang (included in the reaction) anneals to CCC sequence.
- Oligo contains barcode unique to sample and partial Illumina adapter.
- Reverse transcriptase fills in remaining 3' sequence in a process known as template switching.
- Pool samples (96 or greater per plate). Perform PCR with full-length Illumina adapter-containing primers to generate NGS library with unique dual barcodes.

FIG. 27

2% Agarose Gel

- 40: No Biotin, no Biotin Capture
- 41-1: Control
- 41-2: 2% Biotin
- 41-3: 5% Biotin
- 41-4: 10% Biotin

- Note: 41-1 had 50% less loaded DNA on gel

- Direct from lysate (no RNA purification)
- 3 hour workflow (1 hour hands on)
- 384 samples (4x96)
- Unique dual indexes
- Unique molecule indexes
- Strand specific
- 10 cells input (current empirical)

| group | Alignment Summary Metrics | Alignment Summary Metrics | Alignment Summa | Alignment Summary Met | Duplication Metrics (P | Duplication Metrics (Po | Gc Bias Sum | Gc Bias Sum | Insert Size Metrics | Insert Size Metrics |
|---|---|---|---|---|---|---|---|---|---|---|
| category | PAIR | PAIR | PAIR | PAIR | None | None | None | None | FR | FR |
| name | Total Reads | Total Reads Aligned | HQ Error Rate | % Reads Aligned in Pairs | Duplication Rate (Post | Estimated Library Size ( | AT Dropout | GC Dropout | Median Insert Size | Median Insert Size Absolute Deviation |
| 01-DUDI-gold19_S19_L001 | 6534138 | 0.980527 | 0.010468 | 0.983259 | 0.01016 | 170351935 | 3.106843 | 11.009327 | 221 | 32 |
| 02-DUDI-gold19_S19_L001 | 4796732 | 0.989114 | 0.009739 | 0.991022 | 0.011198 | 110832033 | 3.677543 | 8.348567 | 143 | 34 |
| 03-DUDI-gold19_S19_L001 | 6370218 | 0.991972 | 0.009819 | 0.993803 | 0.014398 | 112711356 | 7.46963 | 6.159332 | 120 | 29 |

FIG. 37

METHODS AND COMPOSITIONS FOR HIGH THROUGHPUT SAMPLE PREPARATION USING DOUBLE UNIQUE DUAL INDEXING

CROSS-REFERENCE

This application is a U.S. National Phase Application of International Application No. PCT/US2020/043146, filed Jan. 20, 2022, which claims the benefit of U.S. Provisional Application No. 62/877,197 filed Jul. 22, 2019 and U.S. Provisional Application No. 62/901,958 filed Sep. 18, 2019, each of which is hereby incorporated by reference in its entirety.

BACKGROUND OF THE INVENTION

Next Generation Sequencers are now capable of generating up to 3000 Gbp of short read sequence data per flow cell. In order to take advantage of this scale of sequencing, multiplexing samples during the sequencing process may be desired. This may be enabled by adding molecular barcodes to DNA libraries for sequencing, and using those barcodes to de-multiplex individual samples for analysis. Library construction methods may include fragmentation, blunt end repair, A-tailing and ligation of universal barcoded adapters. Alternatively, library construction may include non-fragmented preparations such as RipTide and tagmentation approaches such as Nexterra.

SUMMARY OF THE INVENTION

In an aspect, provided herein are methods of preparing a sequencing library from a nucleic acid sample comprising: (a) annealing a first oligonucleotide comprising a first barcode sequence and a first random sequence to said nucleic acid sample. In some cases, the method further comprises (b) extending said first oligonucleotide to obtain a first extension product comprising said first barcode sequence, said first random sequence, and a first sample sequence. In some cases, the method further comprises (c) annealing a second oligonucleotide comprising said first barcode sequence and a second random sequence to said first extension product. In some cases, the method further comprises (d) extending said second oligonucleotide to obtain a second extension product comprising said first barcode sequence, said second random sequence, and a complement of said first sample sequence, thereby obtaining a first double-stranded extension product comprising said first extension product and said second extension product. In some cases, the method further comprises (e) attaching a third oligonucleotide comprising a second barcode to said first extension product and a fourth oligonucleotide comprising said second barcode to said second extension product. In some cases, said first barcode is specific to said nucleic acid sample. In some cases, said second barcode is specific to a set of nucleic acid samples. In some cases, said extending is effected using a strand-displacing polymerase. In some cases, said extending is effected using a reverse transcriptase. In some cases, said first random sequence and said second random sequence comprise a GC content appropriate for said nucleic acid sample. In some cases, said first and second extension products comprise a length of about 100 to about 200 bases. In some cases, the method further comprises purifying said first double-stranded extension product. In some cases, the method further comprises performing an end-repair reaction on said first double-stranded extension product. In some cases, the method further comprises performing a phosphorylation reaction on said nucleic acid sample. In some cases, the method further comprises subsequent to (d) degrading said nucleic acid sample with a lambda exonuclease. In some cases, the method further comprises performing a phosphorylation reaction on said first double-stranded extension product. In some cases, the method further comprises performing a polyadenylation reaction on said first double-stranded extension product. In some cases, said third oligonucleotide further comprises a reverse complement nucleic acid sequence of said second barcode that forms a hairpin. In some cases, said attaching comprises ligating. In some cases, said attaching comprises a chemical conjugation. In some cases, the method further comprises performing PCR on the product of step (e). In some cases, the method further comprises adding a sequencing adapter to said double-stranded extension product. In some cases, the method further comprises subjecting said double-stranded extension product to sequencing. In some cases, said nucleic acid sample comprises genomic DNA that has not been fragmented. In some cases, said nucleic acid sample comprises RNA. In some cases, the method further comprises in step (a) annealing a fifth oligonucleotide comprising said first barcode sequence and a first primer sequence and in step (c) annealing a sixth oligonucleotide comprising said first barcode sequence and a second primer sequence, wherein said first primer sequence and said second primer sequence are configured to anneal to a target sequence.

In another aspect, there are provided methods of preparing a sequencing library from a nucleic acid sample comprising: (a) annealing a first oligonucleotide comprising a first barcode sequence and a first primer sequence to said nucleic acid sample. In some cases, the method further comprises (b) extending said first oligonucleotide to obtain a first extension product comprising said first barcode sequence, said first primer sequence, and a first target sequence. In some cases, the method further comprises (c) annealing a second oligonucleotide comprising said first barcode sequence and a second primer sequence to said first extension product. In some cases, the method further comprises (d) extending said second oligonucleotide to obtain a second extension product comprising said first barcode sequence, said second primer sequence, and said first target sequence, thereby obtaining a first double-stranded extension product comprising said first extension product and said second extension product. In some cases, the method further comprises (e) attaching a third oligonucleotide comprising a second barcode to said first extension product and said second extension product. In some cases, said first barcode is specific to said nucleic acid sample. In some cases, said second barcode is specific to a set of nucleic acid samples. In some cases, said extending is effected using a strand-displacing polymerase. In some cases, said extending is effected using a reverse transcriptase. In some cases, said first primer sequence and said second primer sequence comprise a GC content appropriate for said nucleic acid sample. In some cases, said first and second extension products comprise a length of about 100 to about 200 bases. In some cases, the method further comprises purifying said first double-stranded extension product. In some cases, the method further comprises performing an end-repair reaction on said first double-stranded extension product. In some cases, the method further comprises performing a phosphorylation reaction on said nucleic acid sample. In some cases, the method further comprises subsequent to (d) degrading said nucleic acid sample with a lambda exonuclease. In some cases, the method further comprises performing a phosphorylation reaction on said first double-stranded extension product. In some cases, the method further comprises performing a polyadenylation reaction on said first double-stranded extension product. In some cases, said third oligonucleotide further comprises a reverse complement nucleic acid sequence of said second barcode that forms a hairpin. In some cases, said attaching comprises ligating. In some cases, said attaching comprises a chemical conjugation. In some cases, the method further comprises performing PCR on the product of step (e). In some cases, the method further comprises adding a sequencing adapter to said double-stranded extension product. In some cases, the method further comprises subjecting said double-stranded extension product to sequencing. In some cases, said nucleic acid sample comprises genomic DNA that has not been fragmented. In some cases, said nucleic acid sample comprises RNA. In some cases, the method further comprises in step (a) annealing a fifth oligonucleotide comprising said first barcode sequence and a first random sequence and in step (c) annealing a sixth oligonucleotide comprising said first barcode sequence and a second random sequence.

In another aspect, there are provided methods of multiplexing a sequencing library from a plurality of nucleic acid samples comprising: (a) annealing a first plurality of oligonucleotides to a nucleic acid sample of said plurality of nucleic acid samples, wherein each of said first plurality of oligonucleotides comprises (i) a unique barcode sequence corresponding to said nucleic acid sample and (ii) a random sequence capable of base pairing with at least one sequence in said nucleic acid sample. In some cases, the method further comprises (b) extending said first plurality of oligonucleotides to obtain a first plurality of extension products, wherein each of said first plurality of extension products comprises (i) said unique barcode sequence corresponding to said nucleic acid sample and (ii) a sample sequence. In some cases, the method further comprises (c) annealing a second plurality of oligonucleotides to said first plurality of extension products, wherein each of said second plurality of oligonucleotides comprises (i) said unique barcode corresponding to said nucleic acid sample and (ii) a random sequence capable of base pairing with at least one sequence in said first plurality of extension products. In some cases, the method further comprises (d) extending said second plurality of oligonucleotides to obtain a second plurality of extension products, wherein each of said second plurality of extension products comprises (i) said unique barcode sequence corresponding to said nucleic acid sample and (ii) said sample sequence, thereby obtaining a plurality of double-stranded extension products corresponding to said nucleic acid sample, each comprising a member of said first plurality of extension products and a member of said second plurality of extension products. In some cases, the method further comprises (e) pooling each of said plurality of double-stranded extension products corresponding to each of said nucleic acid samples to form a pool of amplified nucleic acid samples. In some cases, the method further comprises (f) ligating a unique barcode sequence corresponding to said pool of amplified nucleic acid samples to each of the plurality of double-stranded extension products of said pool of amplified nucleic acid samples. In some cases, said extending is effected using a strand-displacing polymerase. In some cases, said extending is effected using a reverse transcriptase. In some cases, said random sequence comprises a GC content appropriate for said nucleic acid sample. In some cases, said plurality of extension products comprise a length of about 100 to about 200 bases. In some cases, the method further comprises purifying said plurality of double-stranded extension products. In some cases, the method further comprises performing an end-repair reaction on said plurality of double-stranded extension products. In some cases, the method further comprises performing a phosphorylation reaction on said nucleic acid sample. In some cases, the method further comprises subsequent to (d) degrading said plurality of nucleic acid sample with a lambda exonuclease. In some cases, the method further comprises performing a phosphorylation reaction on said plurality of double-stranded extension products. In some cases, the method further comprises performing a polyadenylation reaction on said plurality of double-stranded extension products. In some cases, said unique barcode sequence corresponding to said pool of amplified nucleic acid samples further comprises a reverse complement nucleic acid sequence of said unique barcode that forms a hairpin. In some cases, said attaching comprises ligating. In some cases, said attaching comprises a chemical conjugation. In some cases, the method further comprises performing PCR on the product of step (f). In some cases, the method further comprises adding a sequencing adapter to said plurality of double-stranded extension products. In some cases, the method further comprises subjecting said plurality of double-stranded extension products to sequencing. In some cases, said plurality of nucleic acid samples comprises genomic DNA that has not been fragmented. In some cases, said nucleic acid sample comprises RNA. In some cases, the method further comprises in step (a) annealing a third plurality of oligonucleotides comprising said first barcode sequence and a first primer sequence; and in step (c) annealing a fourth plurality of oligonucleotides comprising said first barcode sequence and a second primer sequence, wherein said first primer sequence and said second primer sequence are configured to anneal to a target sequence.

In another aspect, there are provided methods of multiplexing a sequencing library from a plurality of nucleic acid samples comprising: (a) annealing a first plurality of oligonucleotides to a nucleic acid sample of said plurality of nucleic acid samples, wherein each of said first plurality of oligonucleotides comprises (i) a unique barcode sequence corresponding to said nucleic acid sample and (ii) a first targeted primer sequence capable of base pairing with at least one target sequence in said nucleic acid sample. In some cases, the method further comprises (b) extending said first plurality of oligonucleotides to obtain a first plurality of extension products, wherein each of said first plurality of extension products comprises (i) said unique barcode sequence corresponding to said nucleic acid sample and (ii) said target sequence. In some cases, the method further comprises (c) annealing a second plurality of oligonucleotides to said first plurality of extension products, wherein each of said second plurality of oligonucleotides comprises (i) said unique barcode corresponding to said nucleic acid sample and (ii) a second targeted primer sequence capable of base pairing with said at least one target sequence in said first plurality of extension products. In some cases, the method further comprises (d) extending said second plurality of oligonucleotides to obtain a second plurality of extension products, wherein each of each of said second plurality of extension products comprises (i) said unique barcode sequence corresponding to said nucleic acid sample and (ii) said target sequence, thereby obtaining a plurality of double-stranded extension products corresponding to said target sequence in said nucleic acid sample, each comprising a member of said first plurality of extension products and a member of said second plurality of extension products. In some cases, the method further comprises (e) pooling each of said plurality of double-stranded extension products corresponding to each of said nucleic acid samples to form a pool of amplified nucleic acid samples. In some cases, the method further comprises (f) ligating a unique barcode sequence to each of the plurality of double-stranded extension products of said pool of amplified nucleic acid samples. In some cases, said extending is effected using a strand-displacing polymerase. In some cases, said extending is effected using a reverse transcriptase. In some cases, said first primer sequence and said second primer sequence comprise a GC content appropriate for said nucleic acid sample. In some cases, said first and second extension products comprise a length of about 100 to about 200 bases. In some cases, the method further comprises purifying said plurality of double-stranded extension products. In some cases, the method further comprises performing an end-repair reaction on said plurality of double-stranded extension products. In some cases, the method further comprises performing a phosphorylation reaction on said nucleic acid sample. In some cases, the method further comprises subsequent to (d) degrading said nucleic acid sample with a lambda exonuclease. In some cases, the method further comprises performing a phosphorylation reaction on said plurality of double-stranded extension products. In some cases, the method further comprises performing a polyadenylation reaction on said plurality of double-stranded extension products. In some cases, said unique barcode sequence corresponding to said pool of amplified nucleic acid samples further comprises a reverse complement nucleic acid sequence of said unique barcode that forms a hairpin. In some cases, said attaching comprises ligating. In some cases, said attaching comprises a chemical conjugation. In some cases, the method further comprises performing PCR on the product of step (f). In some cases, the method further comprises adding a sequencing adapter to said plurality of double-stranded extension products. In some cases, the method further comprises sequencing said plurality of double-stranded extension products. In some cases, said plurality of nucleic acid samples comprises genomic DNA that has not been fragmented. In some cases, said nucleic acid sample comprises RNA. In some cases, the method further comprises in step (a) annealing a third plurality of oligonucleotides comprising said first barcode sequence and a random sequence and in step (c) annealing a fourth plurality of oligonucleotides comprising said first barcode sequence and second random sequence.

In further aspects, there are provided kits comprising a plurality of sample barcoded primers, a universal mastermix, and a plurality of double-stranded dual barcoded adapters. In some cases, the kit further comprises a strand displacing polymerase. In some cases, the kit further comprises a reverse transcriptase. In some cases, the kit further comprises a buffer and dNTPs. In some cases, the kit further comprises sequencing adapters.

In additional aspects, there are provided nucleic acid molecules comprising a first adapter sequence, a forward plate barcode sequence, a forward sample barcode sequence, a sample sequence, a reverse sample barcode, a reverse plate barcode.

In further aspects, there are provided compositions comprising: (a) a sample nucleic acid; (b) a first plurality of oligonucleotides comprising a first barcode sequence and a random sequence; wherein at least one of said plurality of oligonucleotides is at least partially base paired to said sample nucleic acid; and (c) a second plurality of oligonucleotides comprising a second barcode sequence. In some cases, the composition further comprises a strand displacing polymerase and a buffer. In some cases, the composition further comprises a reverse transcriptase and a buffer. In some cases, said second plurality of oligonucleotides comprises a hairpin. In some cases, said sample nucleic acid comprises genomic DNA that has not been fragmented. In some cases, said sample nucleic acid comprises RNA.

In additional aspects, there are provided methods of preparing a sequencing library from a nucleic acid sample comprising: (a) contacting a transpososome comprising a first barcode sequence and a first random sequence to said nucleic acid sample to generate a population of tagged fragments. In some cases, the method further comprises (b) pooling said population of tagged fragments. In some cases, the method further comprises (c) attaching a second barcode to said tagged fragmented template to generate the sequencing library. In some cases, said first barcode is specific to said nucleic acid sample. In some cases, said second barcode is specific to a set of nucleic acid samples. In some cases, said population of tagged fragments comprise a length of about 100 to about 200 bases. In some cases, the method further comprises purifying said population of tagged fragments. In some cases, the method further comprises performing an end-repair reaction on said population of tagged fragments. In some cases, the method further comprises performing a phosphorylation reaction on said nucleic acid sample. In some cases, the method further comprises subsequent to (d) degrading said nucleic acid sample with a lambda exonuclease. In some cases, the method further comprises performing a phosphorylation reaction on said population of tagged fragments. In some cases, the method further comprises performing a polyadenylation reaction on said population of tagged fragments. In some cases, the method further comprises performing PCR on the product of step (c). In some cases, the method further comprises adding a sequencing adapter to said population of tagged fragments. In some cases, the method further comprises subjecting said sequencing library to sequencing. In some cases, said nucleic acid sample comprises genomic DNA that has not been fragmented. In some cases, said nucleic acid sample comprises RNA. In some cases, said attaching comprises ligating. In some cases, said attaching comprises a chemical conjugation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which:

FIG. 4 shows an example of sample and plate indexing.

FIG. 5 shows an example method with pre-amplification of target loci.

FIG. 6 shows an example of sequence quality data obtained using the method herein compared with conventional methods.

FIG. 7 shows GC bias in sequences obtained from samples prepared using methods herein.

FIG. 23 shows chemical ligation template generation.

FIG. 27 shows template switching method of template generation.

FIG. 37 shows data from 3 library pools of 96 samples.

DETAILED DESCRIPTION OF THE INVENTION

Figure 1:
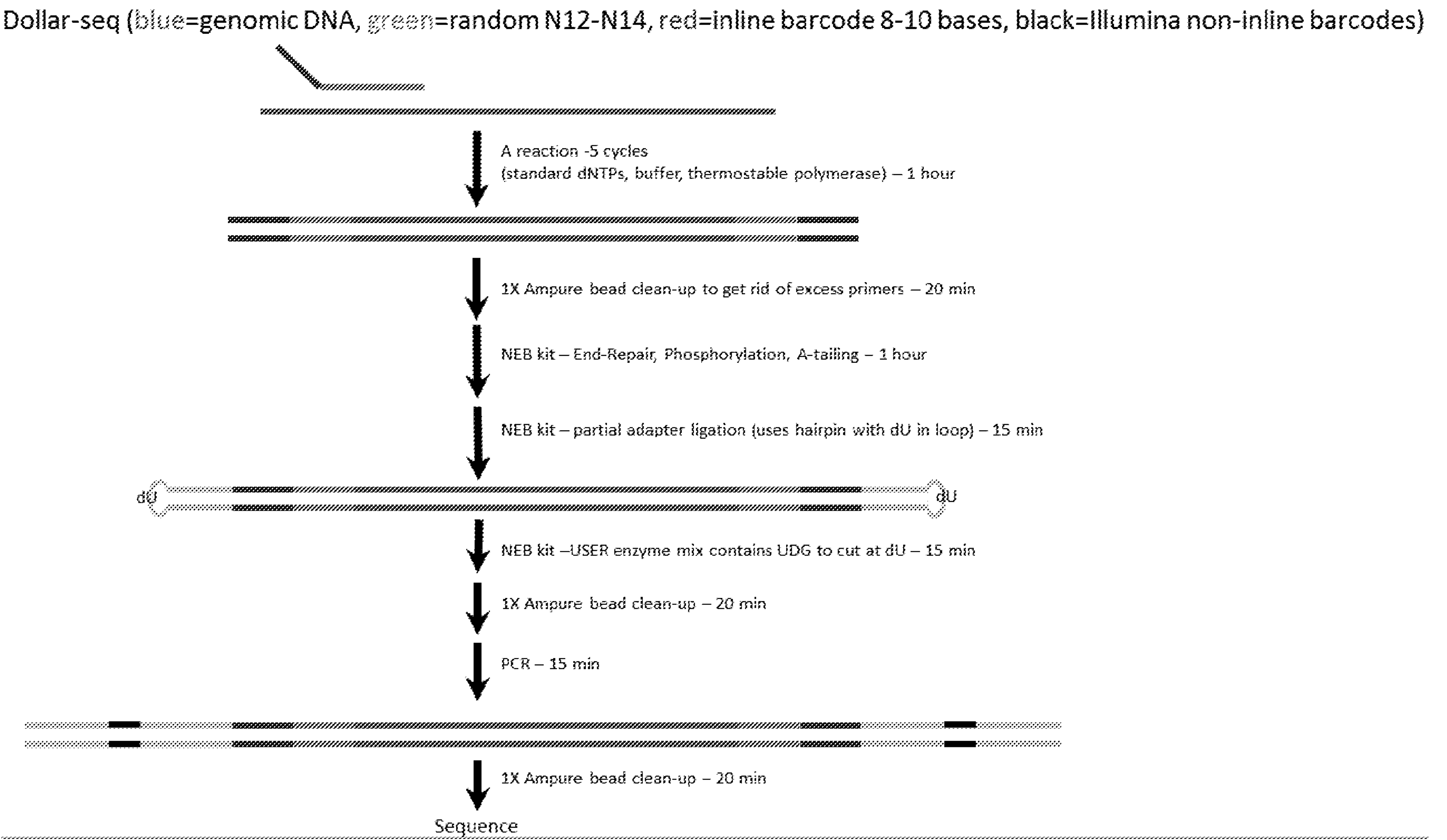
FIG. 1 shows an example sample preparation method using double unique dual indexing.

Next Generation Sequencers are capable of generating up to 3000 Gbp of short read sequence data per flow cell. Multiplexing samples during the sequencing process may take advantage of this scale of sequencing. Adding molecular barcodes to DNA libraries for sequencing, and using those barcodes to de-multiplex individual samples for analysis may allow for such multiplexing. In many cases, library construction methods include fragmentation, blunt end repair, A-tailing, and ligation of universal barcoded adapters. This process may be cumbersome and time consuming if all steps are performed on individual samples. In addition, this process has two major modes of error. The first is due to the fragmentation of the DNA templates. This causes loss of information from an individual molecule (fragments that are two short or too long are removed from the final library) as well as physical damage to the DNA that causes base change errors. The second error mode is known as index hopping or barcode swapping. This occurs when the barcode that is supposed to be assigned to one sample shifts to that of another sample. There are multiple mechanisms that appear to be the cause of index hopping. First, synthesis: during synthesis, a truncated barcode plus an error in the barcode sequencing can cause a barcode to "drift" to that of another similar barcode sequence. Second, excess barcode adapter or primer during amplification either in the library prep or cluster amplification on the sequencer flow cell will shift to another template. Unique Dual Indices (UDIs) may minimize or nearly eliminate barcode hopping from the final data sets.

Provided herein are novel, high throughput library construction methods that avoid fragmentation of the template molecules to be sequenced and allow for DOUBLE Unique Dual Indexing (DUDI) to eliminate barcode hopping across samples and across plates in a highly multiplexed sample preparation. Library construction methods herein are highly advantageous as they enable fragment size selection and dual barcoding in a single tube with little to no manipulation.

The methods described herein and labeled nucleic acid samples can be used to conduct targeted high coverage sequencing in combination with low pass sequencing for imputation. This method is illustrated in FIG. 5. For example, high coverage sequencing (clinical grade) can be achieved with the labeled nucleic acids on the ACMG gene list for reporting results. All of the other 30M+ genotypes can be made in the same assay. Another application would be to cover recombination hotspots that are not imputable and this may allow a user to get to the 99.99% concordance. The genetic recombination and recombination hotspots are described in Mackiewicz, et al., PLOS ONE (Jun. 1, 2013) Volume 8, Issue 6, e65272, p 1-11 and Halldorsson, et al., *Science* 25 Jan. 2019: Vol. 363, Issue 6425, eaau1043, both of which are incorporated by reference in their entireties.

High Throughput Sample Preparation Using Double Unique Dual Indexing

Fragmentation of DNA samples is generally required to obtain molecule lengths that are amenable to cluster generation (clonal amplification) on most sequencing systems. Fragmentation, whether physical or chemical may cause sequence errors in the resulting data, loses information from individual template molecules and requires a number of extensive clean up reactions that limit the ability of most library construction techniques to prepare libraries from low amounts of starting material. It is desirable that a library construction methodology eliminate the need for fragmentation of sample templates. Polymerization is therefore an attractive alternative and can be controlled for product length through various factors including extension times and enzymes used. The use of a 5' barcoded random primer enables each fragment molecule to have a covalently bound molecular barcode to the copies of the template molecules generated. There are a number of considerations in the context of the random primer and the barcode sequence.

Barcodes

Because the primers are synthesized, the length of the barcode may be fixed and always in a known position of the library molecule. Barcode sequences are presented that are designed with 50% GC, no poly-nucleotide adjacent (for example, no AA, CC, TT, GG), are 5'-3' balanced in GC content. Barcodes themselves may be designed for both mismatch tolerance and insertions/deletions, for example truncated oligos during synthesis. Sets of 96, 384, and 1536 are presented that have been empirically determined to amplify with similar efficiency in a pool, and have a hamming distance allowing for at least 2 mismatches with the ability to assign to the correct barcode. The random portion of the primers may be tuned to different GC content depending on the application. For example, a low average GC organism can use a low GC randomer and a high average GC organism can use a high GC randomer. For samples with unknown GC (metagenomic or microbiome) or large genomes with runs of high or low GC, multiple random primer sets with the same barcode may be combined for maximum representation of all levels of GC content in the final library. Pools of random primers may be individually synthesized to represent each of the GC contents specifically for any one genome. Targeted primers may be substituted for random primers in this context. In addition, non-barcoded primer sets may be used in combination with barcoded random primer sets to amplify (simultaneously or in serial) to increase sequencing coverage on certain regions of the genome while minimizing coverage on other regions of the genome. The random portion of the primer may be of fixed or variable length. It has been shown that random sequence at a length of 12-14 bases provides the best footprint for polymerase binding and generates the highest yield and uniformity of the resulting sequence coverage. In addition, for the 96 barcodes used for sample identification, the first four bases of each of the barcodes are critical for cluster identification. Therefore all four bases must be represented in the first four reads in order to have enough diversity to insure accurate cluster identification. In some cases, only random primers are used. Alternatively, a mixture of random and targeted primers may be used. In other cases, only targeted primers are used.

Templates

Because this approach does not fragment the template molecules and require double-stranded inputs for the process, input material may be double or single stranded DNA, cDNA or even RNA where the reaction may be performed as an RT-PCR step in the same tube or in parallel. A sample may contain both RNA and DNA and when using a mix of reverse transcriptase and DNA polymerase can generate double barcoded molecules from both RNA and DNA simultaneously in a sample. For example, methods herein may be used to generate sequencing libraries on all viral, bacterial, fungal and host RNA/DNA found in a sample of blood or CSF.

Polymerase

Ideal characteristics of the polymerase used include: thermal stability to allow for cycling of the reaction, high fidelity to decrease error rates of the system, processivity and strand displacement activity to insure the length and full complementary sequence is generated. An example enzyme is KOD exo-. For simultaneous RNA/DNA library construction, an enzyme can be selected to make a library of both. In some cases, an enzyme that allows for RNA and DNA to be converted simultaneously, such as MasterAmp™ Tth DNA Polymerase. Alternatively or in combination, the polymerase can be a reverse transcriptase.

Cycling

During the first cycle of the method, a chimeric molecule is generated consisting of 3' complementarity and 5' non-complementary sequence where the 5' sequence is the sample or molecular barcode not found in the genome of interest. The second cycle will generate more of these chimeric molecules and also generate double-stranded copies of the products produced in the first cycle of the reaction. These intermediate molecules are the desired result of the method. Random primers not consumed in the initial cycle will bind along the length of the products produced in the first cycle. The strand displacing aspect of the polymerase insures that a primer bound closer to the 3' end of the first reaction product will displace the primers bound upstream or 5' to the furthest 3' hybridization event. The 3' distal hybridized primer will extend through the 5' barcode of the first cycle products and the 3' end of the first products will extend through the 5' barcode of the second hybridization event, resulting in a double-stranded, blunt ended intermediate molecule with dual unique barcodes, inverted, on both ends of the intermediate molecules. Each subsequent cycle will generate more of the desired intermediate products, where each cycle produces double-stranded, dual unique barcoded intermediate molecules of decreasing length. The number of cycles and the elongation time along with the strand displacement produces the majority of intermediate molecules within the desired length of the sequencing system being used. Further, fragment length may be tunable due to polymerization conditions (i.e. extension times and cycle numbers). In some cases, the KOD exo-enzyme adds a poly-A tail, allowing for a separate polyadenylation step to be eliminated from the library preparation workflow.

In the 96-well plate version of the method, 96 samples containing the intermediate dual barcoded products are pooled together in a single tube. Excess primers and reactants from the initial reaction are removed. Intermediate products are repaired, phosphorylated and A-tailed through standard means. Dual unique barcoded adapters are then ligated by standard means. Multiple plates of samples, ligated with different dual unique adapters are then pooled for sequencing. One plate of samples may be processed in about four hours. Multiple plates may be processed simultaneously. By ligating the plate barcode adapters during this step, the possibility of the sample specific barcoded primers from producing any mis-primed or barcode hopped events is eliminated as no polymerase is used.

Priming and Tagmentation Benefits

The random priming approach eliminates the need for fragmenting (breaking covalent bonds) in the template molecules. This eliminates the loss of information due to molecule fragments that are not optimal in size (too short or too long). This should also minimize loss of sensitivity. For example, a molecule of interest in a low percentage of total molecules (such as a somatic event or mosaic event) the information from that molecule could be lost if that region of the molecule is lost. The priming approach allows for multiple samplings of the template molecule, or in other words, multiple independent samplings from the same event, which adds both confidence and sensitivity. In addition, transposase methods have shown to have bias towards certain sequence motifs, particularly the loss of AT rich regions. The negative from this approach is that you "burn" the number of random synthetic bases from the primer for each read. They happen to be the highest quality positions in the read. The tunability of the random priming approach is also beneficial as the composition of the random primers (high vs. low GC) can tune coverage to GC extremes, or balance the coverage when extremes are combined. In addition, spiking in target specific primers allows for even greater tunability.

The advantage of the tagmentation approach is that we would not burn synthetic sequences at the beginning of each read. It is also a very simple workflow.

Figure 28:
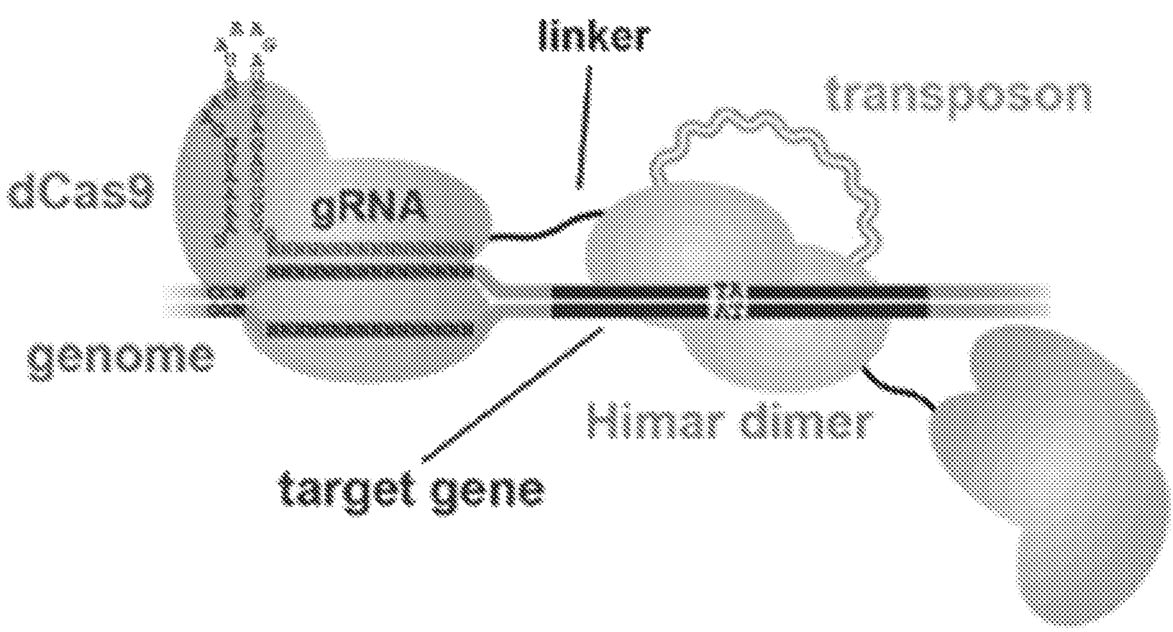
FIG. 28 shows a combination CRISPR/CAS RNA plus transposase template generation.

Alternatively, combination CRISPR/CAS RNA plus transposase conjugates can provide best of both worlds. This is illustrated in FIG. 28. Two references for tethered deactivated CAS and transposase enzymes will be included in this communication: The concept is to use randomly synthesized guide RNAs formed into a ribonucleoprotein complex with deactivated CAS enzymes. The deactivated CAS enzymes are "tethered" to transpososome complexes with unique dual barcodes that are incorporated into template molecules. The random nature of the guide RNAs allow us to "tune" the assay to specific GC content (or even targeted content with specific guide designs on top of it. It also eliminates burying the read bases within the construct. It does not solve the fragmentation issue.

Additional Methods

In some cases, a portion of the library constituents do not have dual barcodes. This may result from genomic DNA template ligation in the second step of the process resulting in products after the random primer reaction that have only one end barcoded and the other end is a blunt end genomic template.

To address this issue, the sample and the adapters may be de-phosphorylated (for example, by using alkaline phosphatase) prior to the ligation reaction. For example, the genomic DNA sample may be treated with alkaline phosphatase, then the reaction may be heat denatured to deactivate the alkaline phosphatase enzyme. Then the barcoding reaction may be performed by cycling with barcoded random primers that are 5' phosphorylated. The adapters may be treated separately with alkaline phosphatase resulting in ligation events that may be only from the 5' ends of the products with primers to the 3' ends of adapters in the ligation reaction, which may be performed on multiple samples simultaneously. The second strand may be filled in through primer extension during the PCR step.

In another aspect of methods herein, the random barcoded primers are swapped with target specific barcoded primers. For example, RT-PCR reactions can be designed targeting a sequence, such as SARS-COV2 diagnostic sequences such as S, N, ORF domains that are tailed with the same sample barcodes. In this example, the forward and reverse primers have the 8 bp sample barcodes and when amplified produce amplicons (from RT-PCR) that have the double unique dual indexes for 96 samples. In some cases, biotinylated dNTPs are used during the reaction to purify the amplicons. Then, in some cases, the 96 samples are pooled, end repaired, a-tailed, and plate specific sequencing adapters are pooled for multiple 96 well plates to be sequenced simultaneously. In some cases, read lengths are quite short. In some cases, each plate is checked through the unique dual indices from the index reads in the standard index position of Illumina sequencing, then read only through the sample barcode and part of the locus specific primers for read 1 and read 2. In some cases, 30 cycles for each direction are performed which can the processing time. In some cases both primers are present within a few hundred base pairs, similar to a fluorescent readout from PCR in that it is highly unlikely that would occur with off target priming. In some cases, a few hundred reads suffice for detection so even the smallest desktop sequencer could process hundreds if not thousands of samples simultaneously in a short turn around time. In some cases, after the initial PCR or RTPCR and prior to pooling, streptavidin coated magnetic beads can be a limiting reagent in each sample to capture an equivalent number of molecules from each sample, pool together to perform end repair, a tail and ligation. Alternatively stubby adapters can be used and PCR to add the plate specific barcodes and universal adapters (full length) for sequencing.

Biotinylated dNTP for Labeling Extension Products

In some cases, an extension product or an amplification product is labeled with a biotinylated dNTP which can incorporate biotin throughout the nucleic acid and in some cases allows for purification of the extension product or amplification product using streptavidin. In some cases, increasing the amount of biotin dNTP affects the insert or fragment length. This can be due to either effects of the biotinylated dNTP on proximity of the biotin molecules in the nucleic acid and/or processivity of the polymerase. For example, with greater biotin incorporation, more biotin molecules in close proximity, in some cases, preferentially binds to the streptavidin beads. In some cases, each streptavidin binds 4 biotins, the proximity of the biotin can factor coming from the same molecule of library and therefore biotins that are closer can be preferentially found to the beads. In some cases, the biotin incorporation would slow down the polymerase during primer extension, and shorter molecules would therefore reach the full length on the reverse strand synthesis more efficiently. In some cases, this can be preferred during PCR amplification.

Instruments and Flow Cells

In aspects of methods herein, a flow cell, an instrument, or a closed system where a sample is input, is used to perform methods herein. In some cases, the library size is controlled to avoid having to do size selection. In some cases, the method is performed on the flow cell or in a microfluidic device that feeds directly into the sequencing flow cell. In some cases, the size selection step is the bottleneck. To avoid size selection, a sample can be input into a chamber where the first rounds of primer extension are performed, then flow into another chamber and capture with streptavidin the desired products while the rest are washed away. Next, in some cases, PCR is used to amplify which would heat denature the streptavidin and release the captured molecules for PCR, which would then flow into the flow cell chamber for bridge amplification.

Normalization

In another aspect, normalizing the number of molecules for each sample in the pool is performed. In some cases, normalization is performed using locked nucleic acids bound to magnetic beads. So after the first step in the cycling reaction, the first strand is synthesized, then the second strand makes a compliment with the same barcode sequence, many times the second barcode will be single stranded. Then, in some cases, the first strand is chewed back to leave a single stranded barcode on the 5' end of the second strand. Next, in some cases, those constructs from the single stranded barcode made are captured during second strand synthesis using the LNA bound to beads as the limiting reagent for each barcode. This would normalize the molecules from each sample going into the ligation step to add sequencing adapters and plate specific barcodes.

Nucleic Acid Molecules and Compositions

Nucleic acid molecules are provided herein comprising a first adapter sequence, a forward plate barcode sequence, a forward sample barcode sequence, a sample sequence, a reverse sample barcode, a reverse plate barcode. Unique barcodes are identical on each end but in inverted orientation on the molecule.

Compositions are also provided herein comprising: (a) a sample nucleic acid; (b) a first plurality of oligonucleotides comprising a first barcode sequence and a random sequence; wherein at least one of the plurality of oligonucleotides is base paired to the sample nucleic acid. In some cases, the composition further comprises a strand displacing polymerase and a buffer. In some cases, the composition further comprises a second plurality of oligonucleotides comprising a second barcode sequence. In some cases, the second plurality of oligonucleotides comprises a hairpin. In some cases, a barcode is used during the amplification step to be included in the index position. In some cases, a barcode is adjacent to the in-line unique dual indexed barcodes in the first priming step.

Kits

Kits may comprise pre-plated or source plates of 96 sample barcoded primers, a universal mastermix, 10 double-stranded dual barcoded adapters and associated materials to generate up to 960 individually barcoded samples. In some cases, kits comprise a module for RNA samples. In some cases, a module for RNA samples is an additional component added to the kit. All materials necessary to go from sample input to a final size selected library may be included in the kit.

Data Analysis

Standard tools for de-multiplexing may be used to identify sequencing reads from individual plates, whereas non-standard demultiplexing of samples within a plate is achieved by reading the first 8 bases from each of the paired end reads on an Illumina sequencer. The random synthetic sequence that is incorporated from the synthetic random primer may be trimmed from the analysis depending on the application. In some cases, the randomer portion of the sequence is trimmed. The randomer may be used as a unique molecular identifier (UMI). In some cases, each fragment yields two reads of the insert plus two index reads.

Derivatives

After the initial sample barcoding reaction that produces a double-stranded unique dual index intermediate, a single adapter and circularization of the products may be implemented. This allows for rolling circle amplification and DNA nano-ball construction for sequencing on platforms such as MGI which uses DNA nanoballs for cluster generation.

Lyophilization of reactants for kit production should allow for a simple "input sample" and add water processing of the initial barcoding reaction.

Process can be done on single cells, in microfluidic devices such as droplets or microchambers or on solid support systems for integrated cluster generation. In addition, bisulfate converted or other modifications to detect DNA methylation may be used as input.

Protected primers may be used in the initial reaction. This can be 5' phosphorylation to enable ligation or a-tailing efficiently. Phosphorthioate or other modifications may be used to protect the intermediate products from exonuclease digestion or click chemistry modifications to enable rapid addition of plate adapters. In some cases, the genomic DNA input sample is degraded after the dual barcoding reaction. In some cases, primers are modified with an affinity motif, such as biotin.

Definitions

A partial list of definitions is as follows.

"Amplified nucleic acid" or "amplified polynucleotide" is any nucleic acid or polynucleotide molecule whose amount has been increased at least two fold by any nucleic acid amplification or replication method performed in vitro as compared to its starting amount. For example, an amplified nucleic acid is obtained from a polymerase chain reaction (PCR) which can, in some instances, amplify DNA in an exponential manner (for example, amplification to $2^n$ copies in n cycles). Amplified nucleic acid can also be obtained from a linear amplification.

"Amplification product" can refer to a product resulting from an amplification reaction such as a polymerase chain reaction.

An "amplicon" is a polynucleotide or nucleic acid that is the source and/or product of natural or artificial amplification or replication events.

The term "biological sample" or "sample" generally refers to a sample or part isolated from a biological entity. The biological sample may show the nature of the whole and examples include, without limitation, bodily fluids, dissociated tumor specimens, cultured cells, and any combination thereof. Biological samples can come from one or more individuals. One or more biological samples can come from the same individual. One non limiting example would be if one sample came from an individual's blood and a second sample came from an individual's tumor biopsy. Examples of biological samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, microbiota, meconium, breast milk and/or other excretions. The samples may include nasopharyngeal wash. Examples of tissue samples of the subject may include but are not limited to, connective tissue, muscle tissue, nervous tissue, epithelial tissue, cartilage, cancerous or tumor sample, or bone. The sample may be provided from a human or animal. The sample may be provided from a mammal, including vertebrates, such as murines, simians, humans, farm animals, sport animals, or pets. The sample may be collected from a living or dead subject. The sample may be collected fresh from a subject or may have undergone some form of pre-processing, storage, or transport.

"Bodily fluid" generally can describe a fluid or secretion originating from the body of a subject. In some instances, bodily fluids are a mixture of more than one type of bodily fluid mixed together. Some non-limiting examples of bodily fluids are: blood, urine, bone marrow, spinal fluid, pleural fluid, lymphatic fluid, amniotic fluid, ascites, sputum, or a combination thereof.

"Complementary" or "complementarity" can refer to nucleic acid molecules that are related by base-pairing. Complementary nucleotides are, generally, A and T (or A and U), or C and G (or G and U). Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100%) complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Hybridization temperatures are generally at least about 2° C. to about 6° C. lower than melting temperatures ($T_m$).

A "barcode" or "molecular barcode" is a material for labeling. The barcode can label a molecule such as a nucleic acid or a polypeptide. The material for labeling is associated with information. A barcode is called a sequence identifier (i.e. a sequence-based barcode or sequence index). A barcode is a particular nucleotide sequence. A barcode is used as an identifier. A barcode is a different size molecule or different ending points of the same molecule. Barcodes can include a specific sequence within the molecule and a different ending sequence. For example, a molecule that is amplified from the same primer and has 25 nucleotide positions is different than a molecule that is amplified and has 27 nucleotide positions. The addition of positions in the 27-mer sequence is considered a barcode. A barcode is incorporated into a polynucleotide. A barcode is incorporated into a polynucleotide by many methods. Some non-limiting methods for incorporating a barcode can include molecular biology methods. Some non-limiting examples of molecular biology methods to incorporate a barcode are through primers (e.g., tailed primer elongation), probes (i.e., elongation with ligation to a probe), or ligation (i.e., ligation of known sequence to a molecule).

A barcode is incorporated into any region of a polynucleotide. The region is known. The region is unknown. The barcode is added to any position along the polynucleotide. The barcode is added to the 5' end of a polynucleotide. The barcode is added to the 3' end of the polynucleotide. The barcode is added in between the 5' and 3' end of a polynucleotide. A barcode is added with one or more other known sequences. One non-limiting example is the addition of a barcode with a sequence adapter.

Barcodes is associated with information. Some non-limiting examples of the type of information a barcode is associated with information include: the source of a sample; the orientation of a sample; the region or container a sample was processed in; the adjacent polynucleotide; or any combination thereof.

In some cases, barcodes are made from combinations of sequences (different from combinatorial barcoding) and is used to identify a sample or a genomic coordinate and a different template molecule or single strand the molecular label and copy of the strand was obtained from. In some cases a sample identifier, a genomic coordinate and a specific label for each biological molecule may be amplified together. Barcodes, synthetic codes, or label information can also be obtained from the sequence context of the code (allowing for errors or error correcting), the length of the code, the orientation of the code, the position of the code within the molecule, and in combination with other natural or synthetic codes.

Barcodes may be added before pooling of samples. When the sequences are determined of the pooled samples, the barcode is sequenced along with the rest of the polynucleotide. The barcode may be used to associate the sequenced fragment with the source of the sample.

Barcodes can also be used to identify the strandedness of a sample. One or more barcodes is used together. Two or more barcodes is adjacent to one another, not adjacent to one another, or any combination thereof.

"Double-stranded" can refer to two polynucleotide strands that have annealed through complementary base-pairing.

"Known oligonucleotide sequence" or "known oligonucleotide" or "known sequence" can refer to a polynucleotide sequence that is known. A known oligonucleotide sequence can correspond to an oligonucleotide that has been designed, e.g., a universal primer for next generation sequencing platforms (e.g., Illumina, 454), a probe, an adaptor, a tag, a primer, a molecular barcode sequence, an identifier. A known sequence can comprise part of a primer. A known oligonucleotide sequence may not actually be known by a particular user but is constructively known, for example, by being stored as data which may be accessible by a computer. A known sequence may also be a trade secret that is actually unknown or a secret to one or more users but may be known by the entity who has designed a particular component of the experiment, kit, apparatus or software that the user is using.

"Library" can refer to a collection of nucleic acids. A library can contain one or more target fragments. In some instances the target fragments are amplified nucleic acids. In other instances, the target fragments are nucleic acid that is not amplified. A library can contain nucleic acid that has one or more known oligonucleotide sequence(s) added to the 3' end, the 5' end or both the 3' and 5' end. The library may be prepared so that the fragments can contain a known oligonucleotide sequence that identifies the source of the library (e.g., a molecular identification barcode identifying a patient or DNA source). In some instances, two or more libraries are pooled to create a library pool. Kits may be commercially available, such as the Illumina NEXTERA kit (Illumina, San Diego, CA).

The term "melting temperature" or "$T_m$" commonly refers to the temperature at which a population of double-stranded nucleic acid molecules becomes half dissociated into single strands. Equations for calculating the $T_m$ of nucleic acids are well known in the art. One equation that gives a simple estimate of the $T_m$ value is as follows: $T_m$=81.5+16.6(log 10[$Na^+$])0.41(%[G+C])−675/n−1.0 m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references can include more sophisticated computations, which take structural as well as sequence characteristics into account for the calculation of $T_m$.

"Nucleotide" can refer to a base-sugar-phosphate combination. Nucleotides are monomeric units of a nucleic acid sequence (e.g., DNA and RNA). The term nucleotide includes naturally and non-naturally occurring ribonucleoside triphosphates ATP, TTP, UTP, CTG, GTP, and ITP, for example and deoxyribonucleoside triphosphates such as dATP, dCTP, dITP, dUTP, dGTP, dTTP, or derivatives thereof. Such derivatives can include, for example, [aS] dATP, 7-deaza-dGTP and 7-deaza-dATP, and, for example, nucleotide derivatives that confer nuclease resistance on the nucleic acid molecule containing them. The term nucleotide as used herein also refers to dideoxyribonucleoside triphosphates (ddNTPs) and their derivatives. Illustrative examples of dideoxyribonucleoside triphosphates include, ddATP, ddCTP, ddGTP, ddITP, ddUTP, ddTTP, for example. Other ddNTPs are contemplated and consistent with the disclosure herein, such as dd (2-6 diamino) purine.

"Polymerase" can refer to an enzyme that links individual nucleotides together into a strand, using another strand as a template.

"Polymerase chain reaction" or "PCR" can refer to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, is amplified to obtain thousands, millions, or billions of replicates. The polymerase chain reaction is used to detect and measure very small amounts of DNA and to create customized pieces of DNA.

The terms "polynucleotides" and "oligonucleotides" may include but is not limited to various DNA, RNA molecules, derivatives or combination thereof. These may include species such as dNTPs, ddNTPs, 2-methyl NTPs, DNA, RNA, peptide nucleic acids, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA. "Oligonucleotides," generally, are polynucleotides of a length suitable for use as primers, generally about 6-50 bases but with exceptions, particularly longer, being not uncommon.

A "primer" generally refers to an oligonucleotide used to prime nucleotide extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific nucleic acid region.

"Primer extension product" or "extension product" used interchangeably herein generally refer to the product resulting from a primer extension reaction using a contiguous polynucleotide as a template, and a complementary or partially complementary primer to the contiguous sequence.

"Sequencing," "sequence determination," and the like generally refers to any and all biochemical methods that may be used to determine the order of nucleotide bases in a nucleic acid.

A "sequence" as used herein refers to a series of ordered nucleic acid bases that reflects the relative order of adjacent nucleic acid bases in a nucleic acid molecule, and that can readily be identified specifically though not necessarily uniquely with that nucleic acid molecule. Generally, though not in all cases, a sequence requires a plurality of nucleic acid bases, such as 5 or more bases, to be informative although this number may vary by context. Thus a restriction endonuclease may be referred to as having a 'sequence' that it identifies and specifically cleaves even if this sequence is only four bases. A sequence need not 'uniquely map' to a fragment of a sample. However, in most cases a sequence must contain sufficient information to be informative as to its molecular source. In some cases, the sequence is a genotype.

The term "biological sample" or "sample" generally refers to a sample or part isolated from a biological entity. The biological sample may show the nature of the whole and examples include, without limitation, bodily fluids, dissociated tumor specimens, cultured cells, and any combination thereof. Biological samples can come from one or more individuals. One or more biological samples can come from the same individual. One non limiting example would be if one sample came from an individual's blood and a second sample came from an individual's tumor biopsy. Examples of biological samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, microbiota, environmental samples, meconium, breast milk and/or other excretions. The samples may include nasopharyngeal wash. In some cases, the sample is for a microbiome analysis. In some cases, the sample comprises a microbe that causes infectious disease, for example, a bacteria, a virus, or a fungus. In some cases, the sample comprises a single cell. In some cases, the sample is a pool of samples from a population of subjects for a population genomics analysis. Examples of tissue samples of the subject may include but are not limited to, connective tissue, muscle tissue, nervous tissue, epithelial tissue, cartilage, cancerous or tumor sample, or bone. The sample may be provided from a human or animal. The sample may be provided from a mammal, including vertebrates, such as murines, simians, humans, farm animals, sport animals, or pets. The sample may be collected from a living or dead subject. The sample may be collected fresh from a subject or may have undergone some form of pre-processing, storage, or transport.

A "subject" generally refers to an organism that is currently living or an organism that at one time was living or an entity with a genome that can replicate. The methods, kits, and/or compositions of the disclosure is applied to one or more single-celled or multi-cellular subjects, including but not limited to microorganisms such as bacterium and yeast; insects including but not limited to flies, beetles, and bees; plants including but not limited to corn, wheat, seaweed or algae; and animals including, but not limited to: humans; laboratory animals such as mice, rats, monkeys, and chimpanzees; domestic animals such as dogs and cats; agricultural animals such as cows, horses, pigs, sheep, goats; and wild animals such as pandas, lions, tigers, bears, leopards, elephants, zebras, giraffes, gorillas, dolphins, and whales. The methods of this disclosure can also be applied to germs or infectious agents, such as viruses or virus particles or one or more cells that have been infected by one or more viruses.

A "support" is solid, semisolid, a bead, a surface. The support is mobile in a solution or is immobile.

The term "unique identifier" may include but is not limited to a molecular bar code, or a percentage of a nucleic acid in a mix, such as dUTP.

A "primer" as used herein refers to an oligonucleotide that anneals to a template molecule and provides a 3' OH group from which template-directed nucleic acid synthesis can occur. Primers comprise unmodified deoxynucleic acids in many cases, but in some cases comprise alternate nucleic acids such as ribonucleic acids or modified nucleic acids such as 2' methyl ribonucleic acids.

As used herein, a nucleic acid is double-stranded if it comprises hydrogen-bonded base pairings. Not all bases in the molecule need to be base-paired for the molecule to be referred to as double-stranded.

The term “about” as used herein in reference to a number refers to that number plus or minus up to 10% of that number. The term used in reference to a range refers to a range having a lower limit as much as 10% below the stated lower limit, and an upper number up to 10% above the stated limit.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Double Unique Dual Indexing Library Generation

Figure 2:
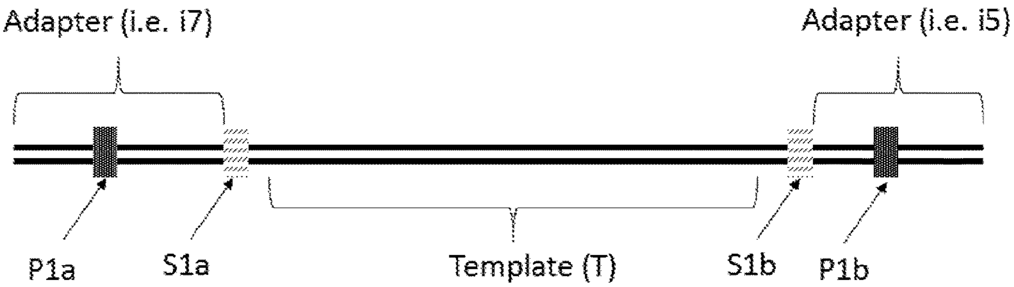
FIG. 2 shows an example Double Unique Dual Index Molecule structure including the flanking the template sequence which also includes synthetic random sequence.
Figure 3:
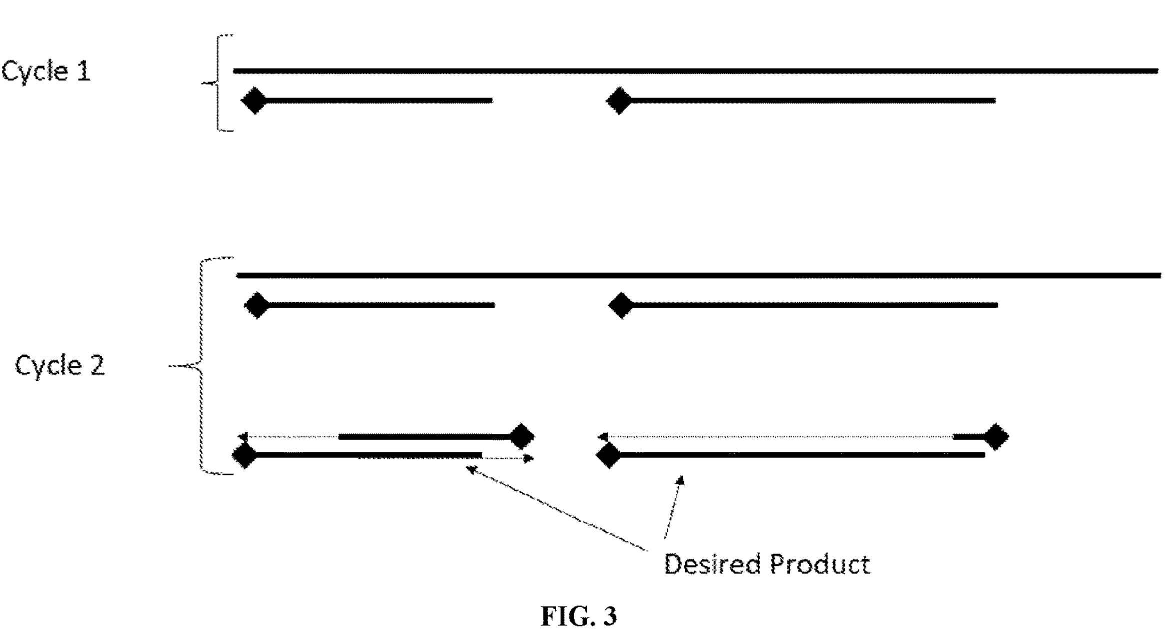
FIG. 3 shows an example of desired products formed by methods of double unique dual indexing after the second cycle.

FIG. 1 shows a summary of a method of double unique dual indexing to arrive at a double labeled library product, such as that shown in FIG. 2. In more detail, sample inputs of genomic DNA (gDNA) are plated in individual wells of a microplate (or other separation device). The DNA templates are heat denatured. Within each well, a random primer with a well/sample specific barcode tail on 5' end (5'-barcode-Nmer-OH-3') is hybridized to the template molecule. A strand displacing polymerase is used to extend the primers from the 3'-OH making an initial copy of the template molecule. Temperature cycling is performed 2 or more times. In the first cycle, primer extension products have a barcode on the 5' end (FIG. 3, top panel). During the second cycle and beyond, double-stranded products are generated to include inverse barcodes on both ends of the desired intermediate molecules (FIG. 3, bottom panel). Elongation times and cycling conditions are tuned to optimize the length of the dual barcoded library molecules. After the desired number of cycles, products from all individual wells of a plate are pooled together in a single tube (FIG. 4). A bead based cleanup removes short molecules and excess primers and reactants. The pooled products are then phosphorylated, end repaired, A-tailed and another set of dual unique barcoded adapters are ligated to produce Double Unique Dual Indexed libraries. Multiple plates processed in the same manner (with different UDI barcoded adapters) can be pooled prior to sequencing. In a 96 well plate example, each well has a random primer (N14) with a different 8 bp 5' barcode specific to each well or sample in the plate. These 96 sample barcodes may be combined with 10 different plate barcodes, resulting in unique dual indexing for each sample in a plate and unique dual indexing for each plate sequenced on the same flow cell. The construct of the library is as follows: P1a-S1a-N12-template-N12-S1b-P1b where P=plate barcode, S=sample barcode, 1=barcode 1, a=forward orientation and b=reverse orientation. In the example where a 96 well plate format is used and ten plates of samples are pooled, then P=1-10 and S=1-96. For the Illumina system, four sequence reads are generated. The plate barcodes are read in the i5, i7 positions of the Illumina adapter sequences while the sample barcodes are read “in-line” with the forward and reverse reads.

Figure 8:
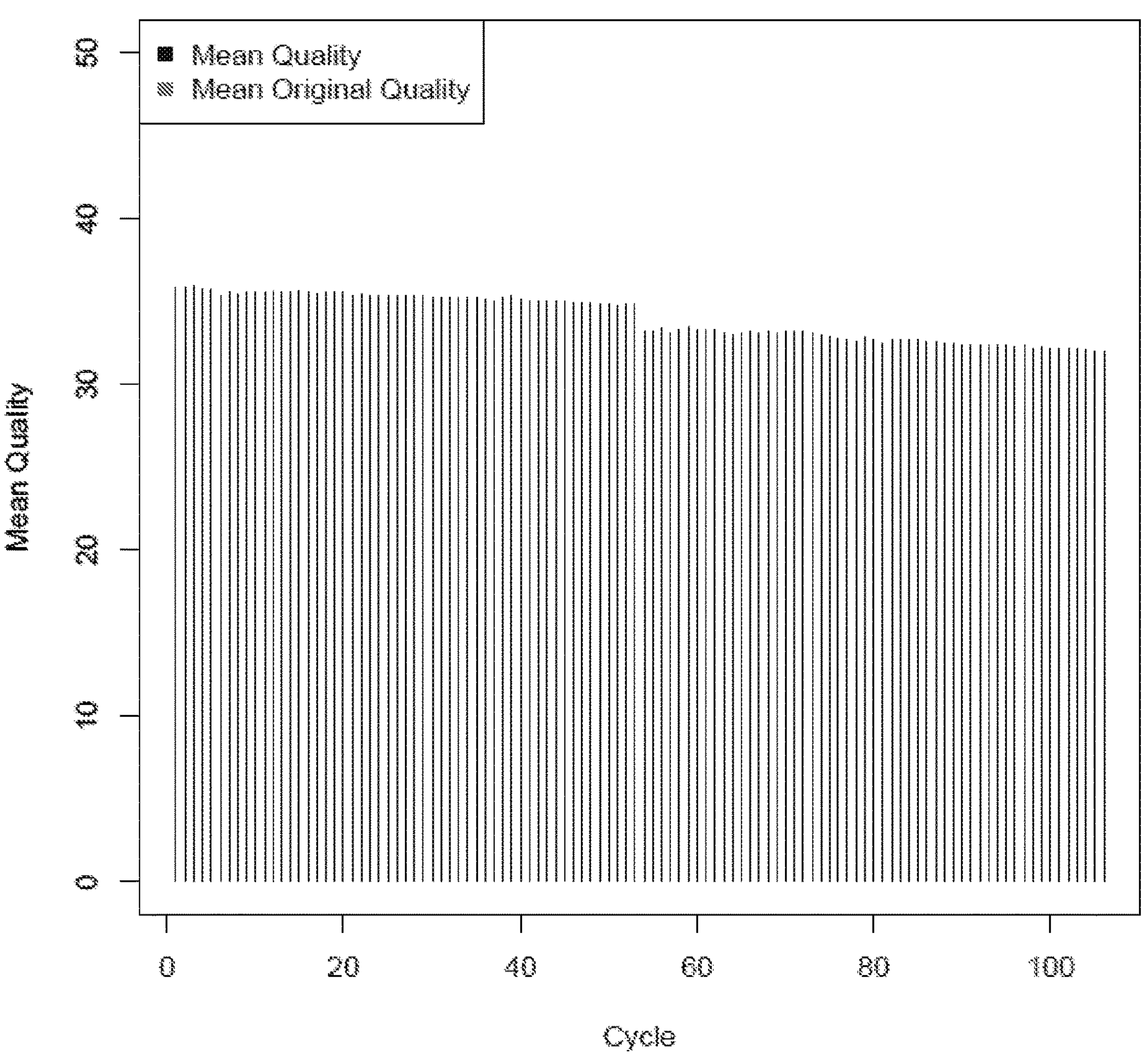
FIG. 8 shows quality scores per cycle in sequences obtained from samples prepared using methods herein.
Figure 9:
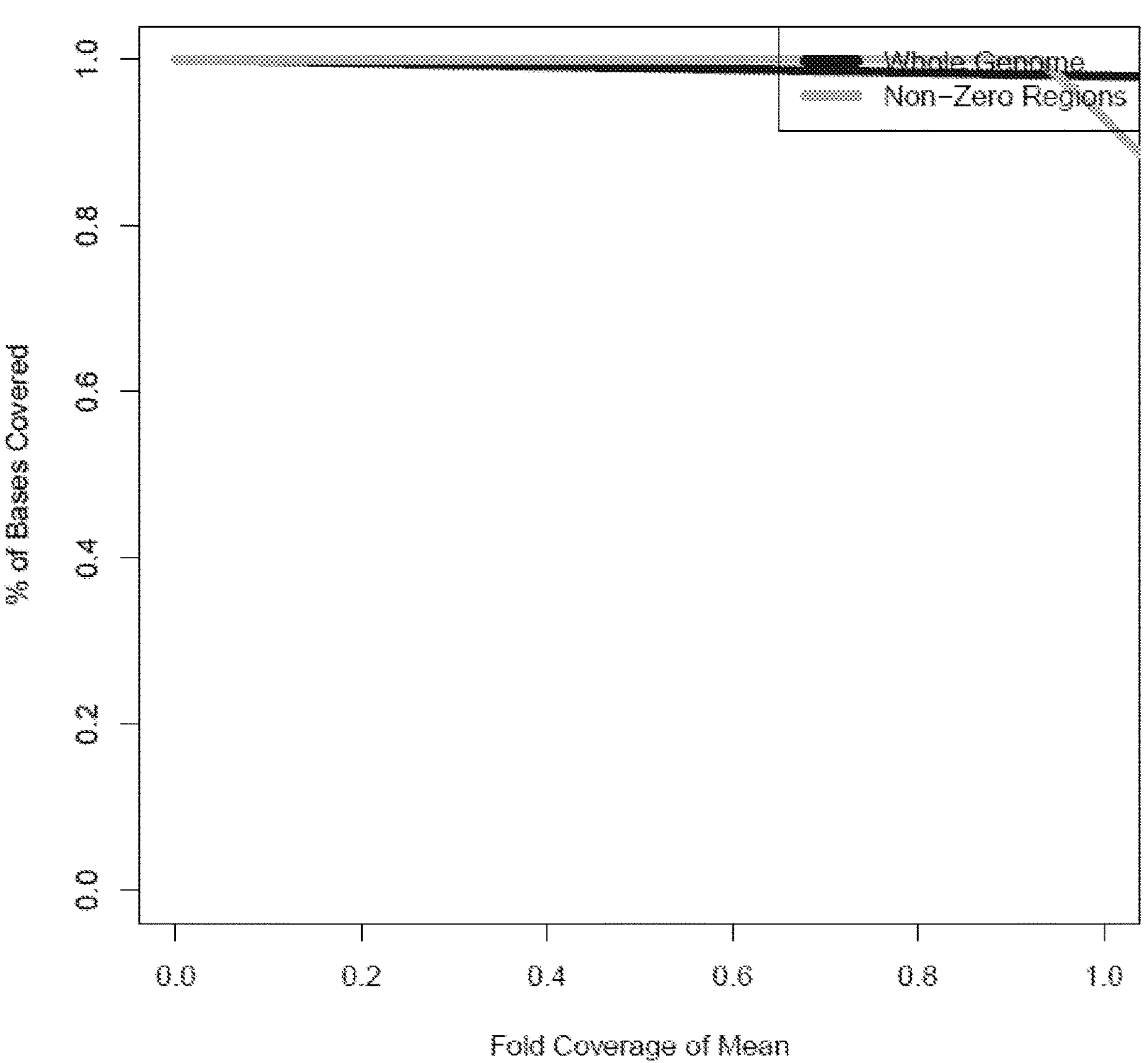
FIG. 9 shows WGS base coverage in sequences obtained from samples prepared using methods herein.
Figure 10:
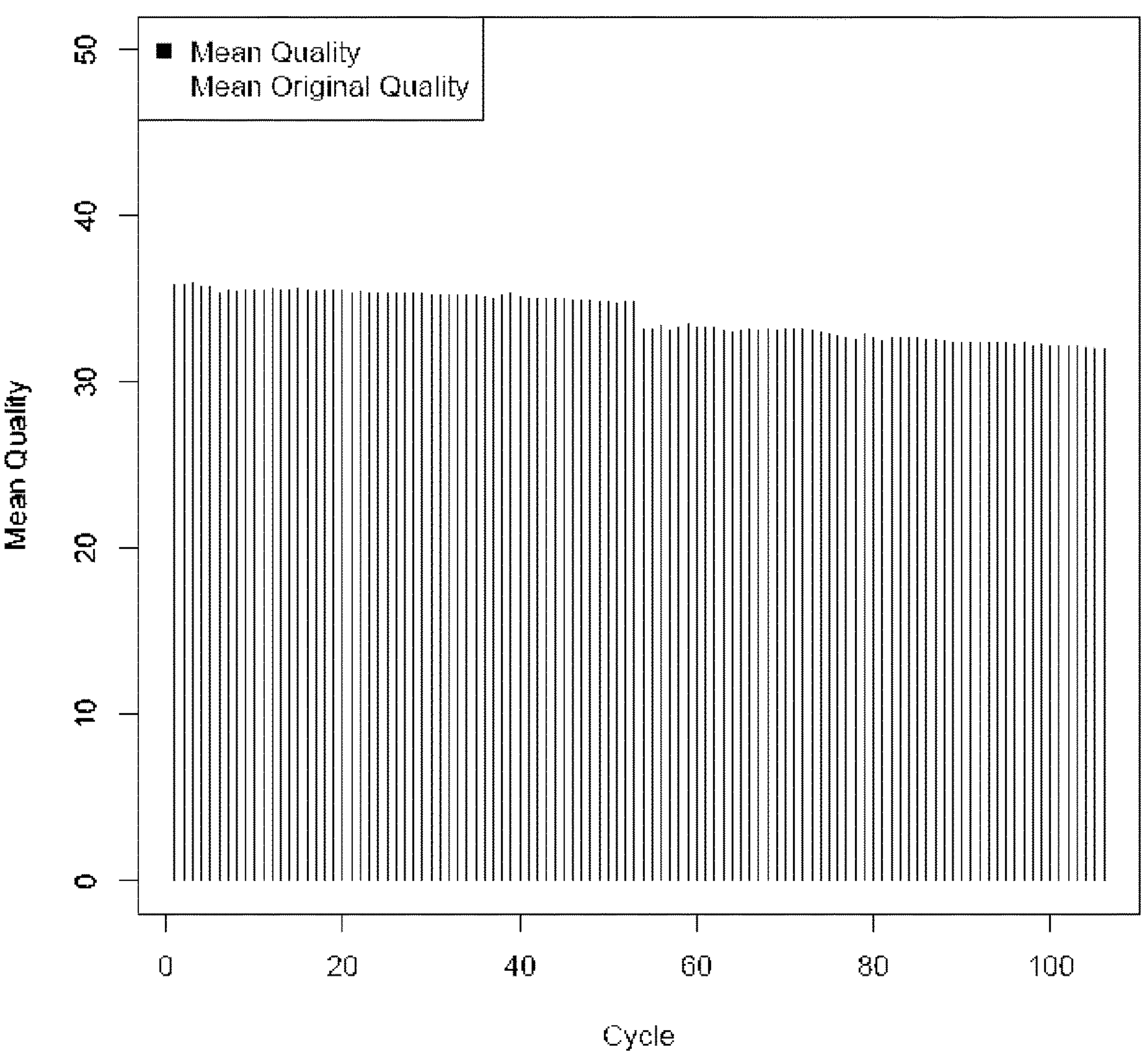
FIG. 10 shows quality scores per cycle in sequences obtained from samples prepared using methods herein.
Figure 11:
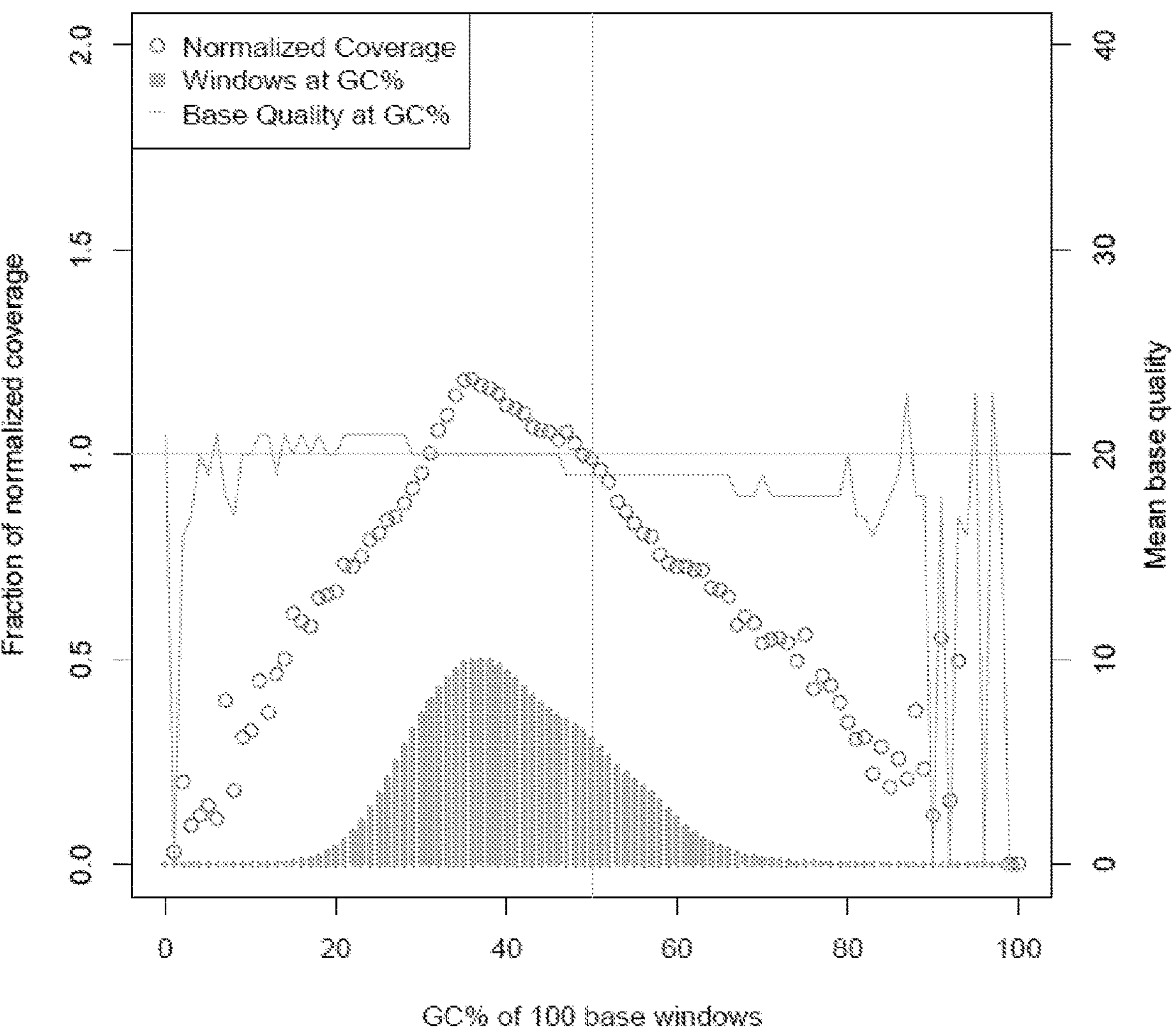
FIG. 11 shows GC bias in sequences obtained from samples prepared using methods herein.
Figure 12:
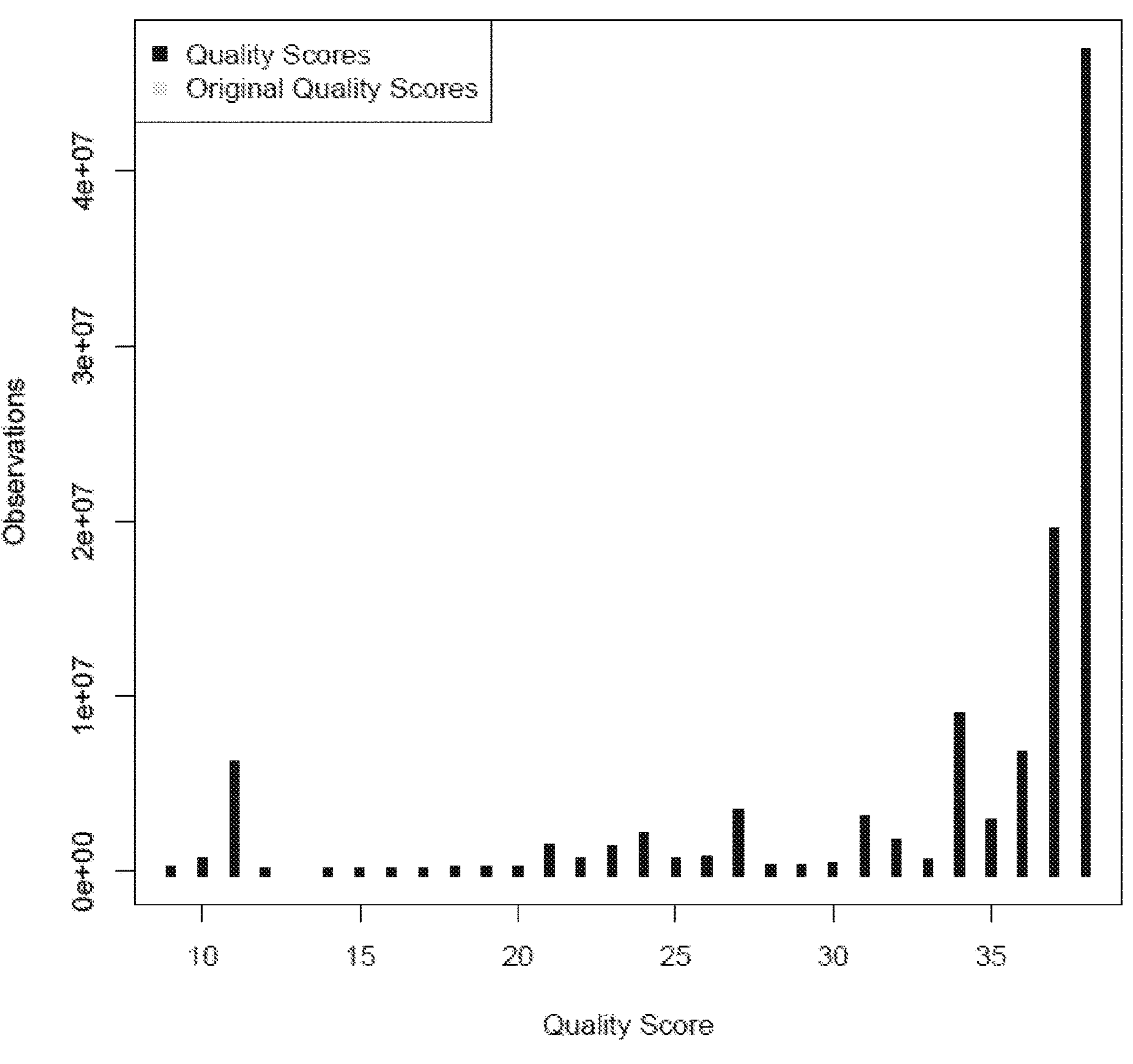
FIG. 12 shows quality score distribution in sequences obtained from samples prepared using methods herein.
Figure 13:
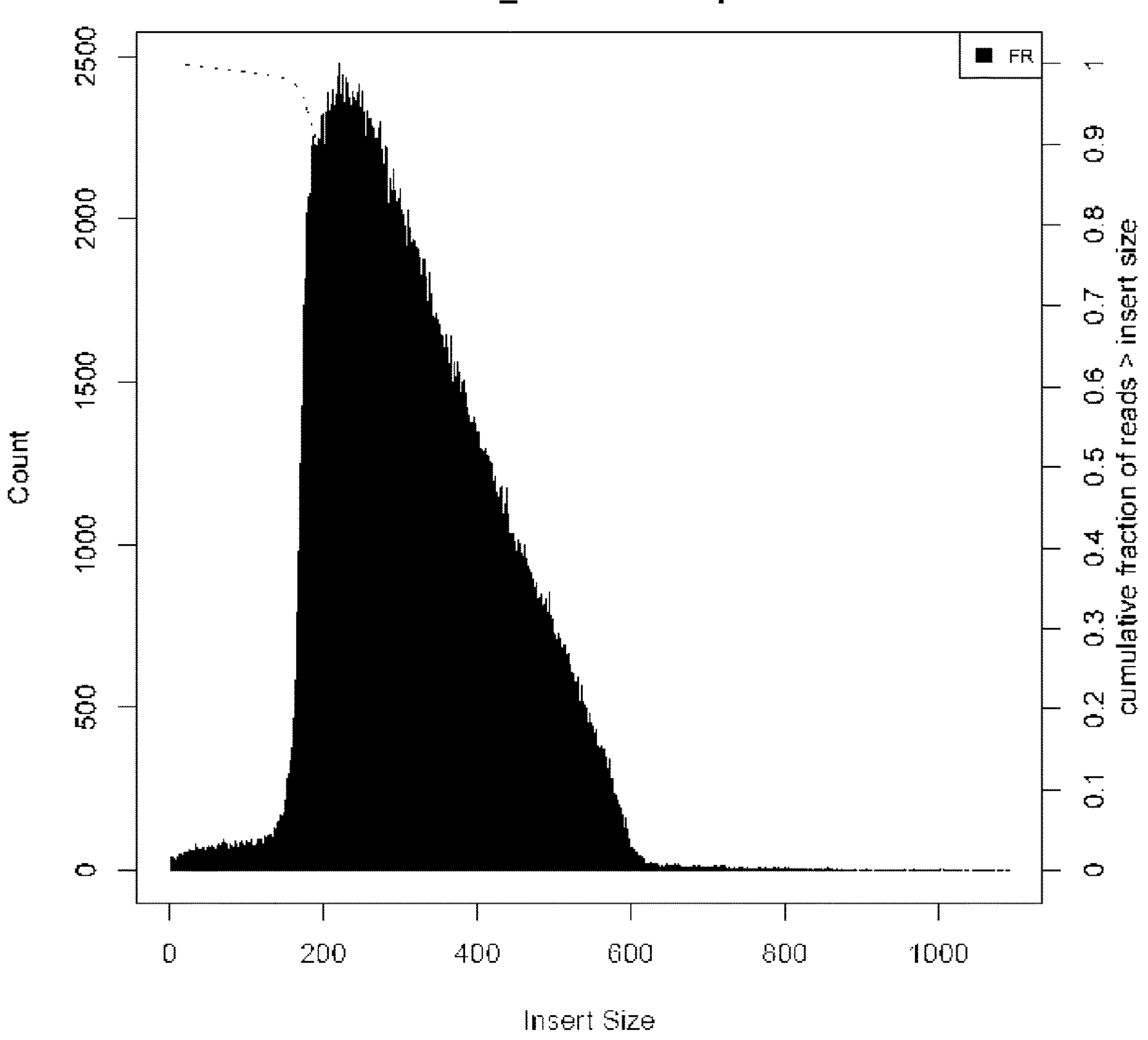
FIG. 13 shows insert size in sequences obtained from samples prepared using methods herein.
Figure 14:
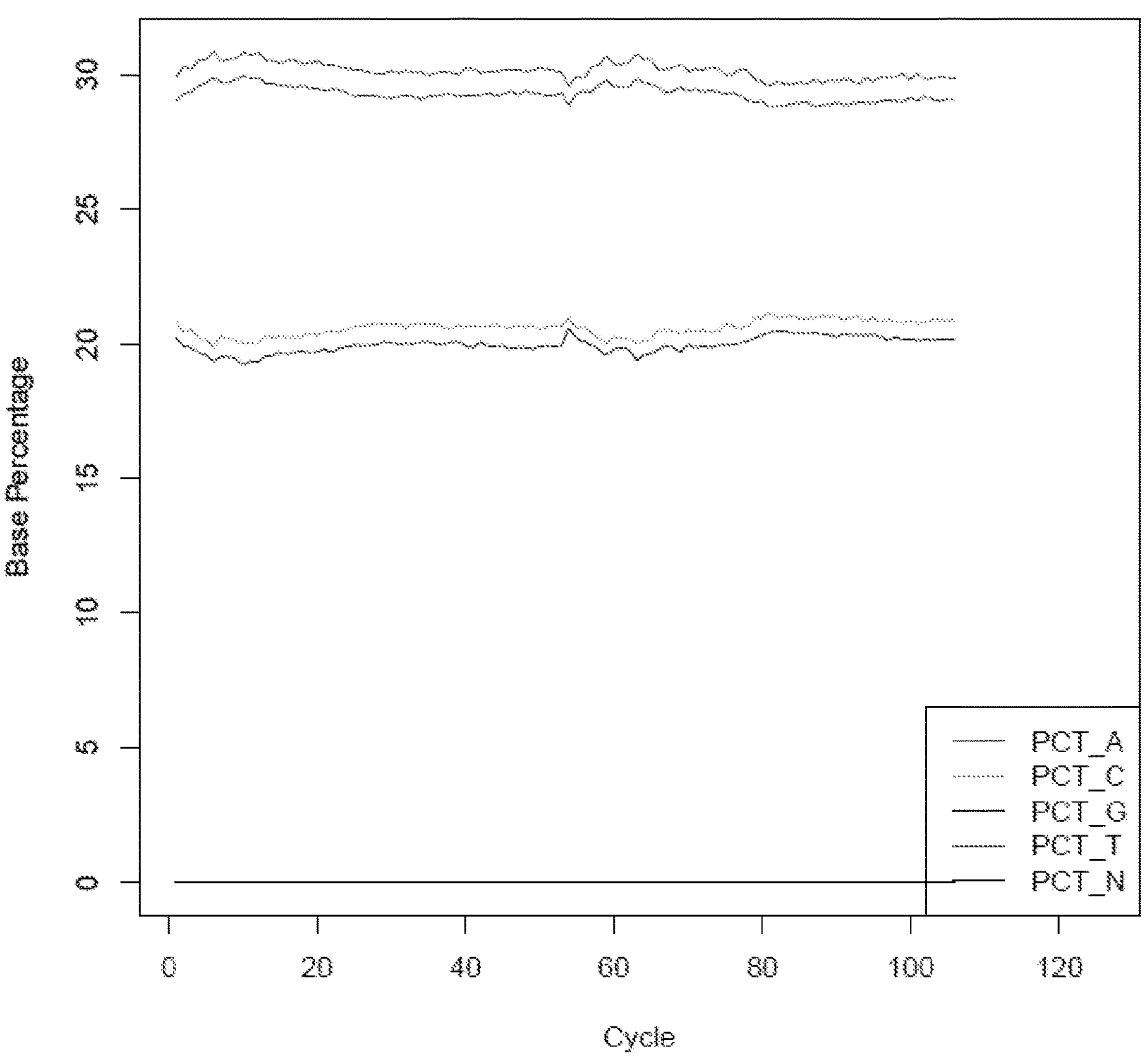
FIG. 14 shows base distribution in sequences obtained from samples prepared using methods herein.
Figure 15:
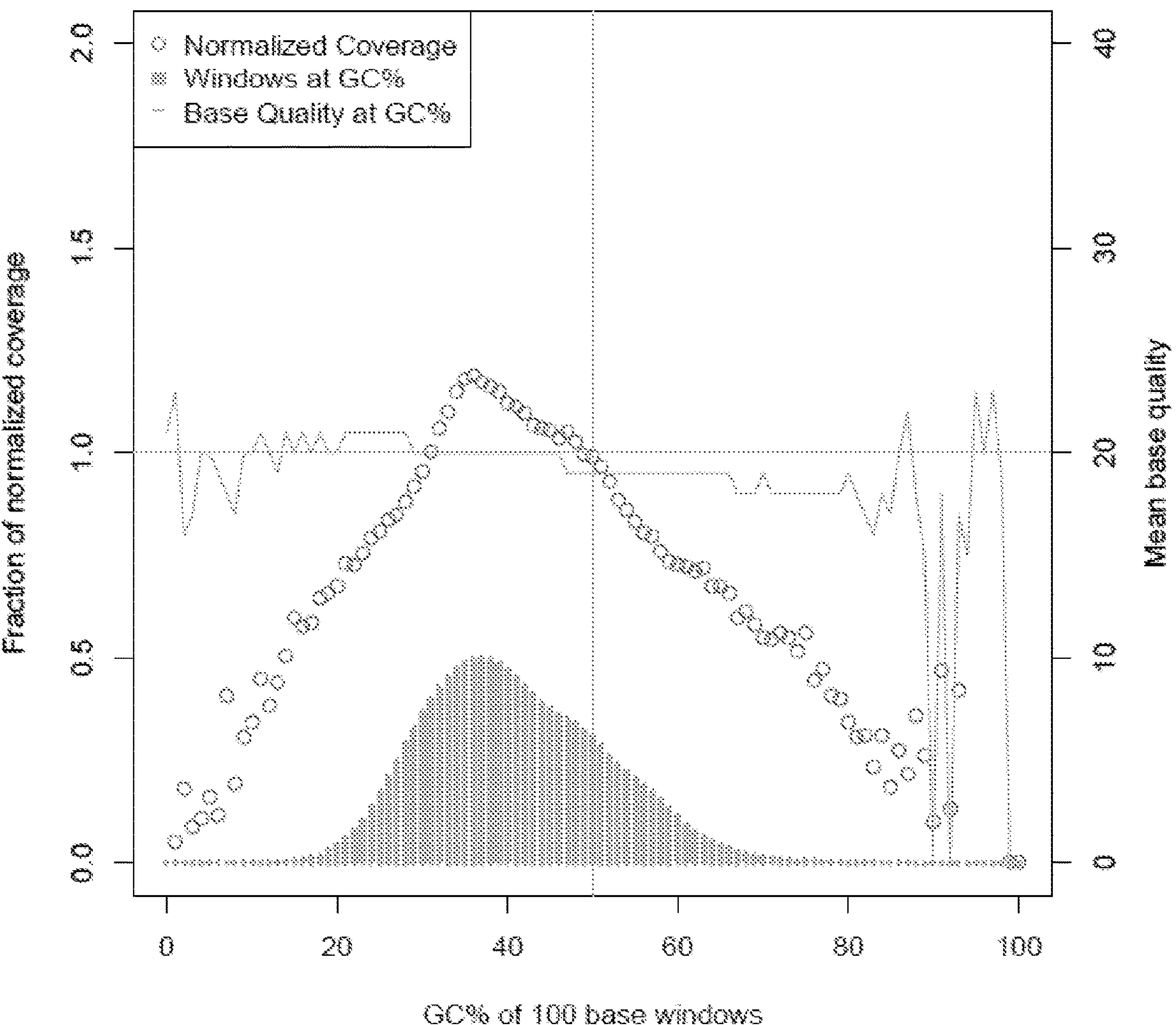
FIG. 15 shows GC bias in sequences obtained from samples prepared using methods herein.
Figure 16:
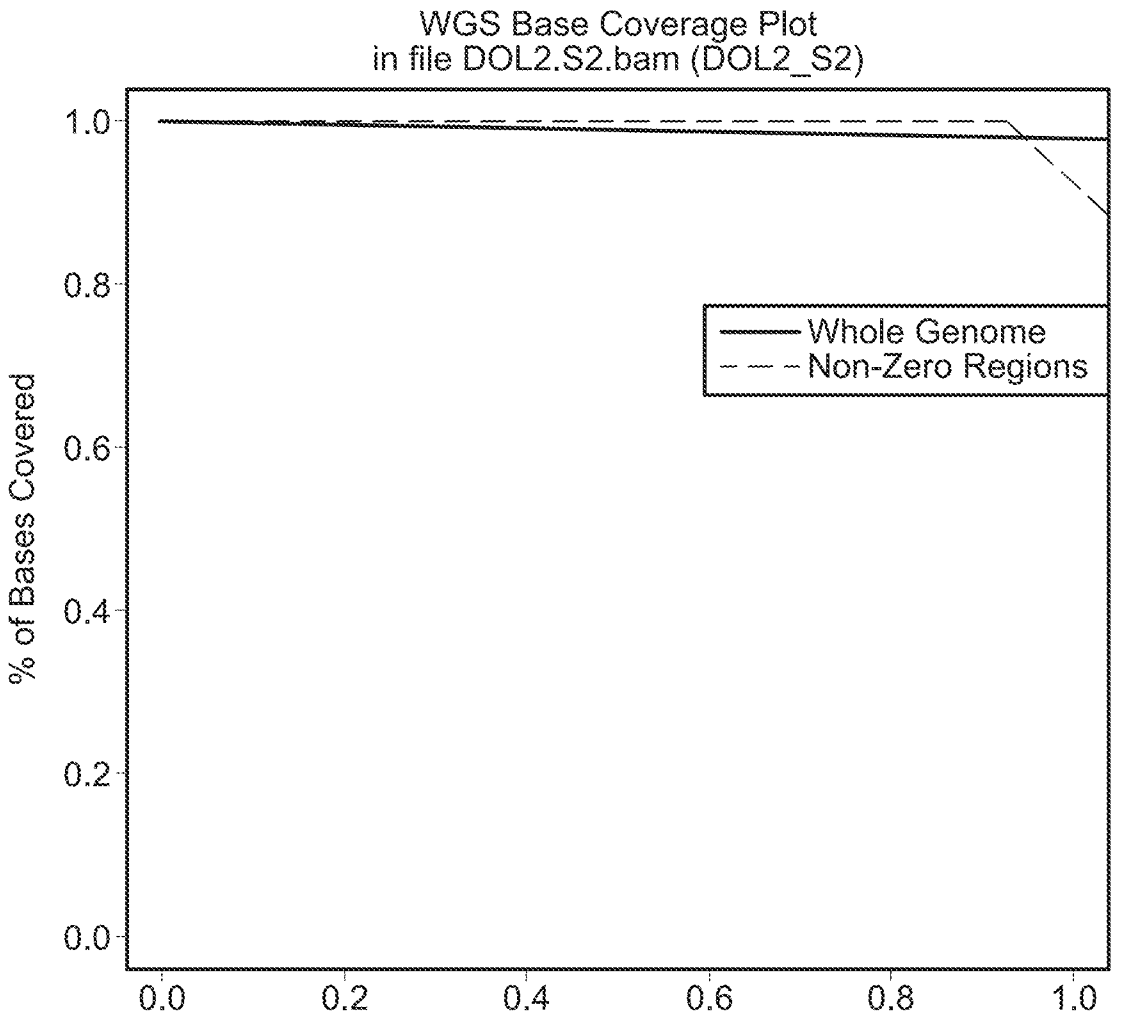
FIG. 16 shows WGS base coverage in sequences obtained from samples prepared using methods herein.
Figure 17:
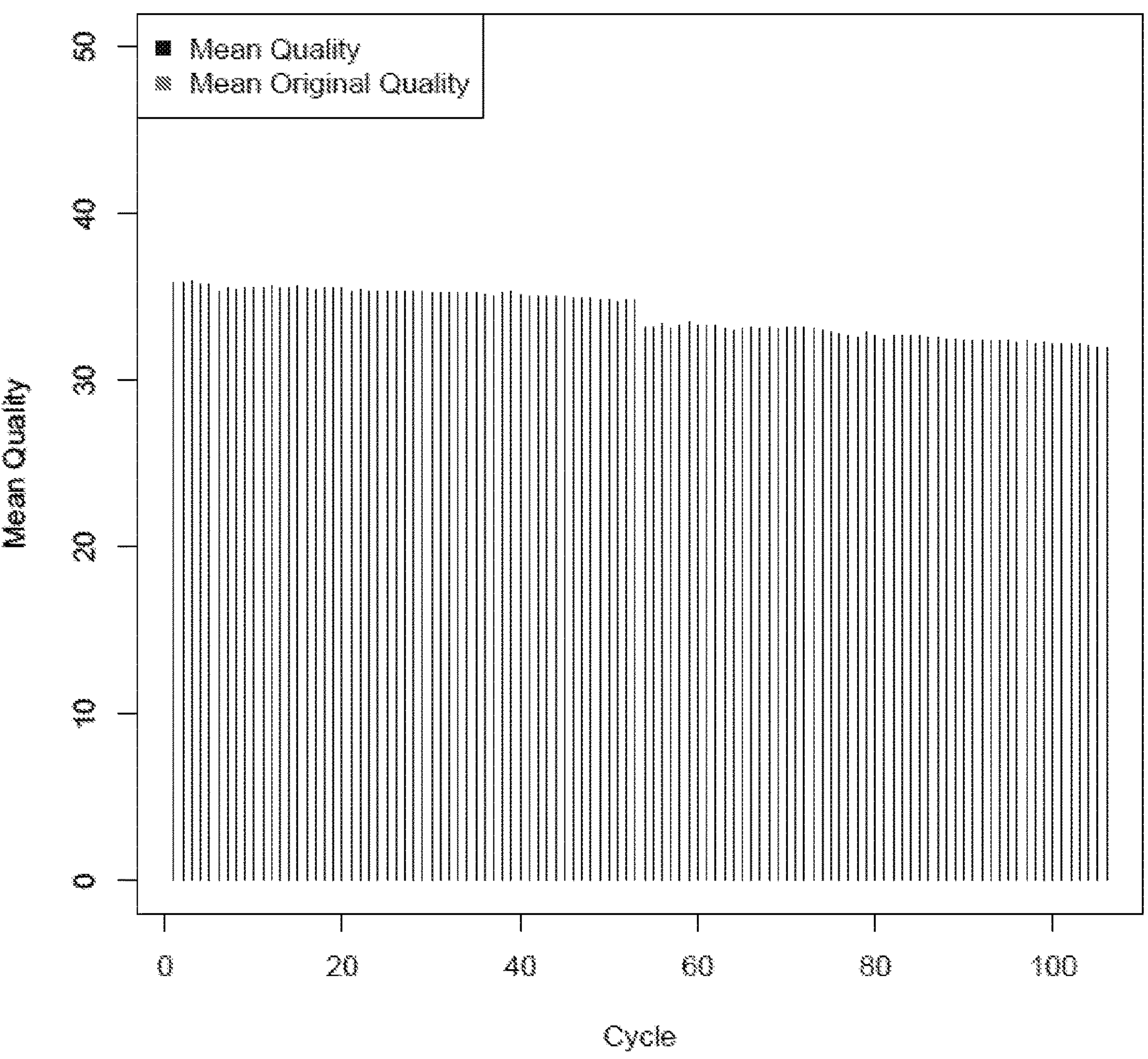
FIG. 17 shows quality scores by cycle in sequences obtained from samples prepared using methods herein.
Figure 18:
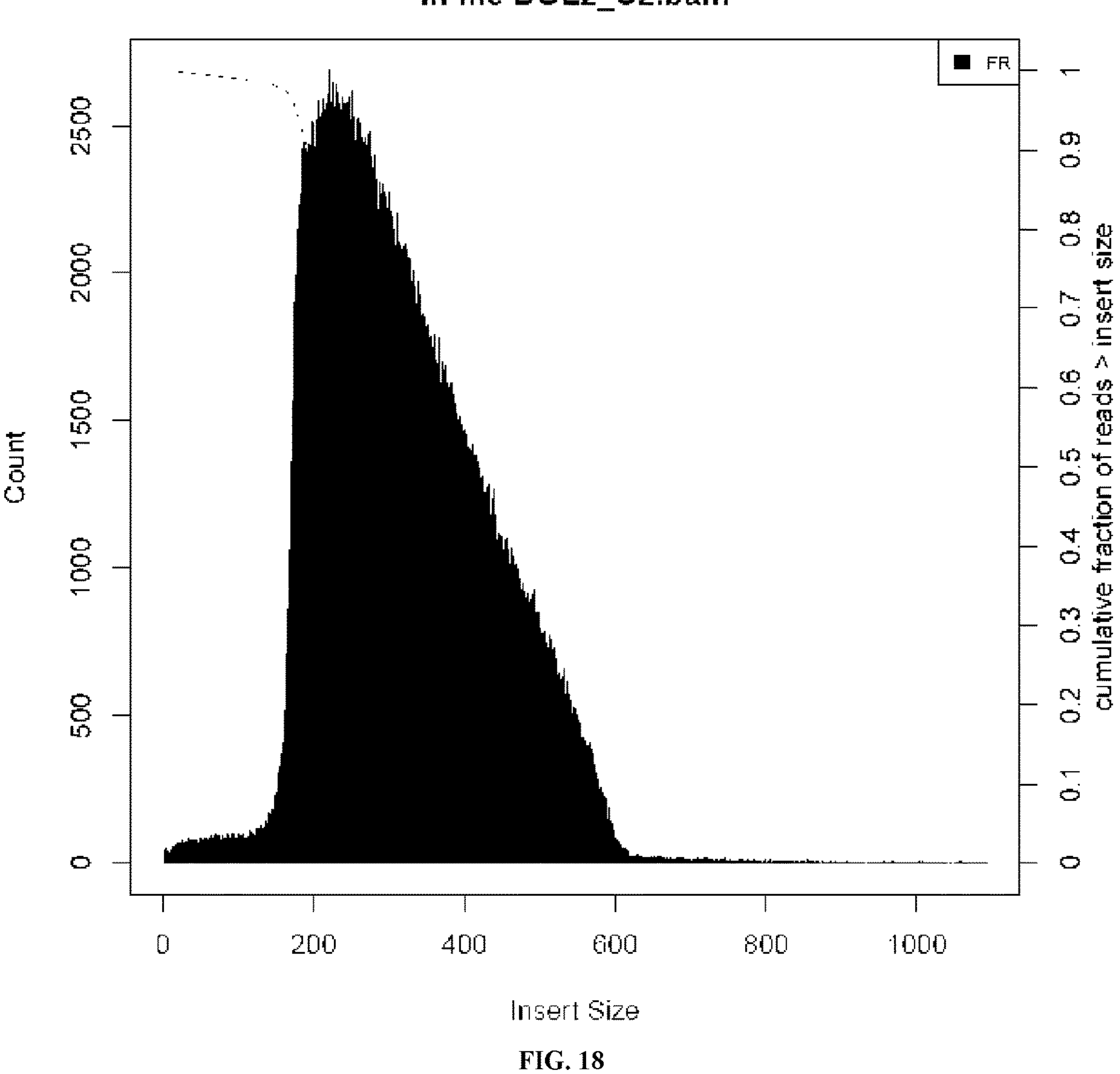
FIG. 18 shows insert size in sequences obtained from samples prepared using methods herein.
Figure 19:
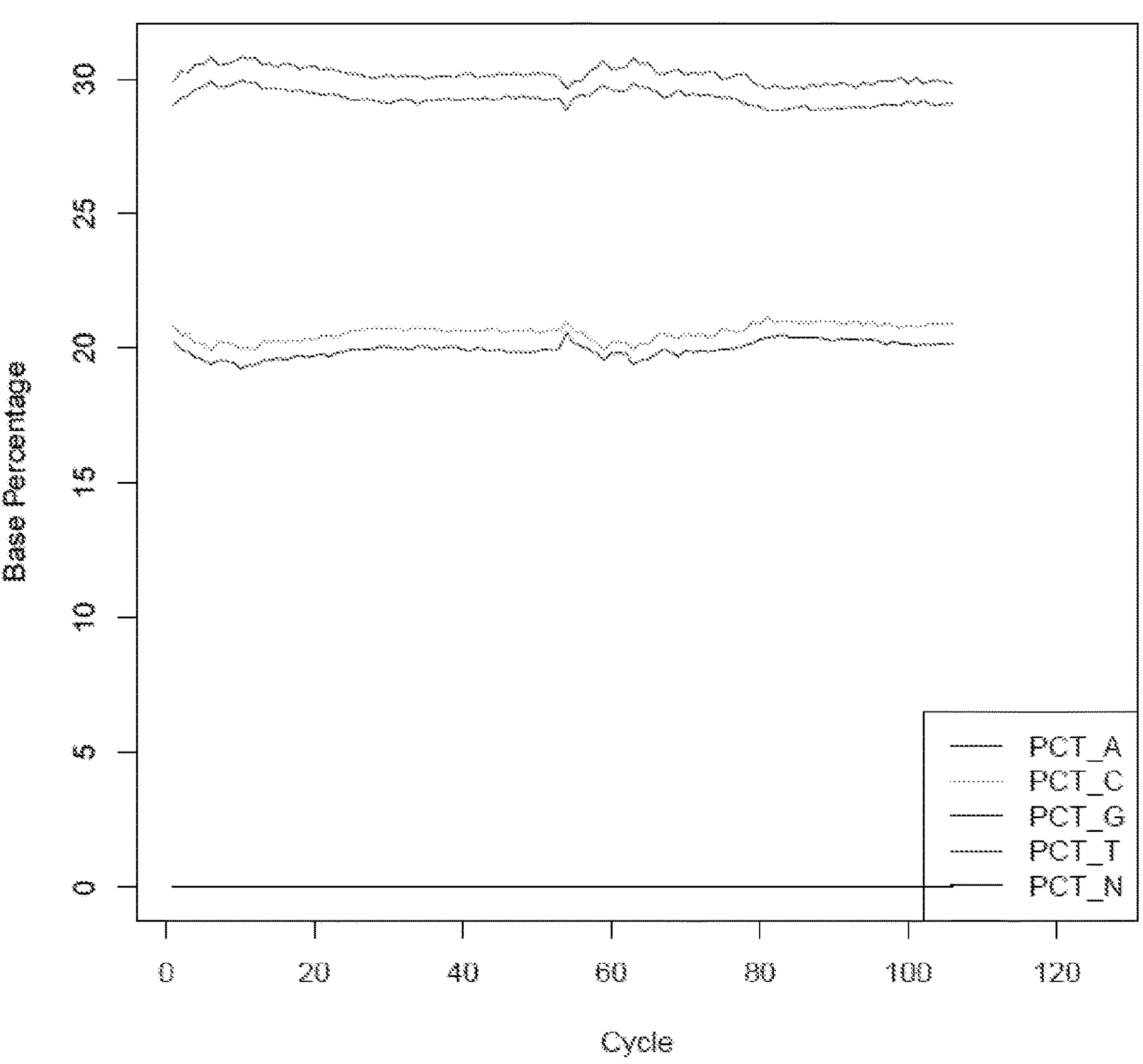
FIG. 19 shows base distribution by cycle in sequences obtained from samples prepared using methods herein.
Figure 20:
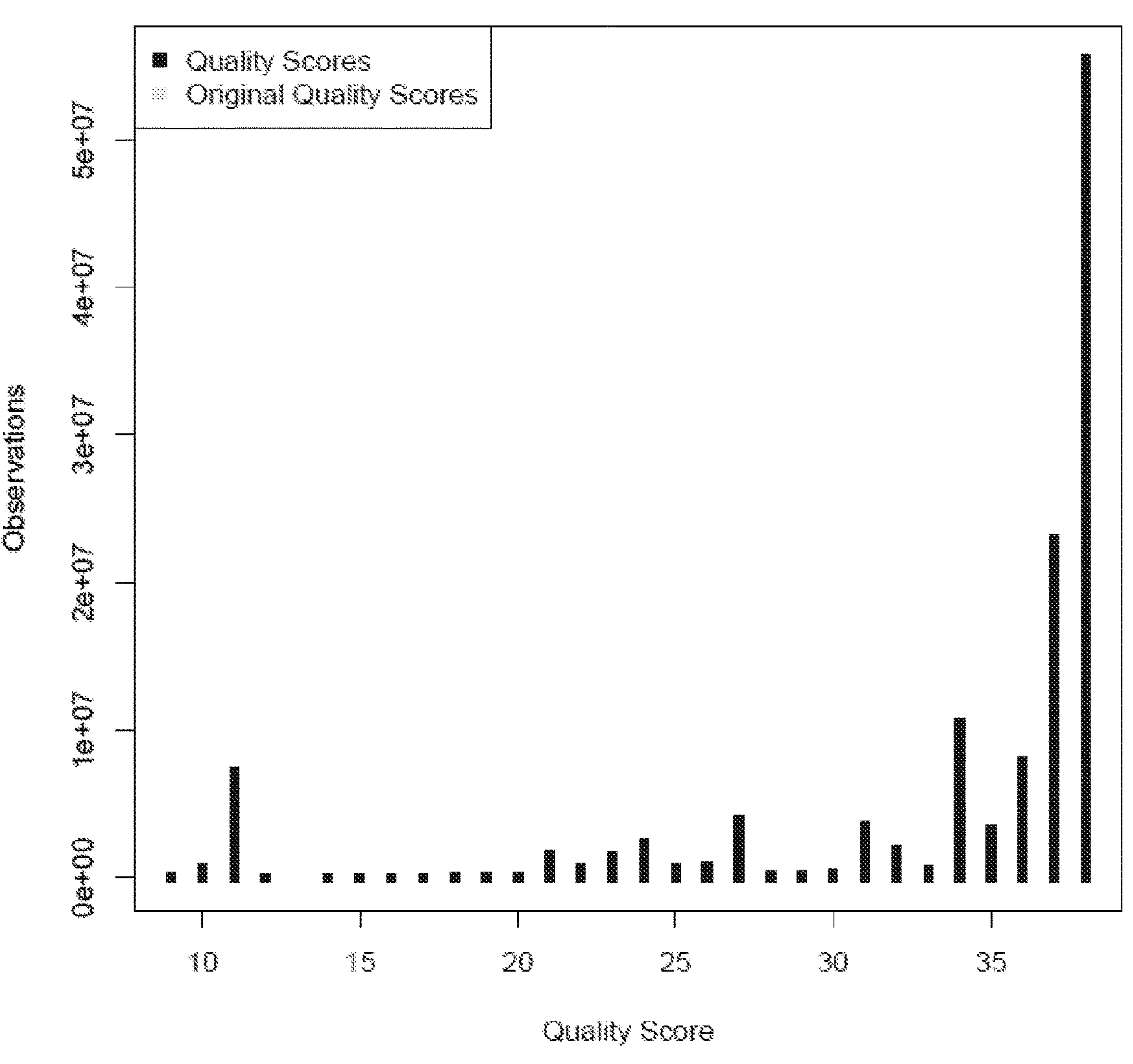
FIG. 20 shows quality score distribution in sequences obtained from samples prepared using methods herein.

Data obtained from sequencing libraries obtained using this method is shown herein. FIG. 6 shows an example of sequence quality data obtained using the method herein compared with conventional methods. FIG. 7 shows GC bias in sequences obtained from samples prepared using methods herein. FIG. 8 shows quality scores per cycle in sequences obtained from samples prepared using methods herein. FIG. 9 shows WGS base coverage in sequences obtained from samples prepared using methods herein. FIG. 10 shows quality scores per cycle in sequences obtained from samples prepared using methods herein. FIG. 11 shows GC bias in sequences obtained from samples prepared using methods herein. FIG. 12 shows quality score distribution in sequences obtained from samples prepared using methods herein. FIG. 13 shows insert size in sequences obtained from samples prepared using methods herein. FIG. 14 shows base distribution in sequences obtained from samples prepared using methods herein. FIG. 15 shows GC bias in sequences obtained from samples prepared using methods herein. FIG. 16 shows WGS base coverage in sequences obtained from samples prepared using methods herein. FIG. 17 shows quality scores by cycle in sequences obtained from samples prepared using methods herein. FIG. 18 shows insert size in sequences obtained from samples prepared using methods herein. FIG. 19 shows base distribution by cycle in sequences obtained from samples prepared using methods herein. FIG. 20 shows quality score distribution in sequences obtained from samples prepared using methods herein.

Example 2: Template Generation Using Exo$^-$ Polymerase

Figure 21:
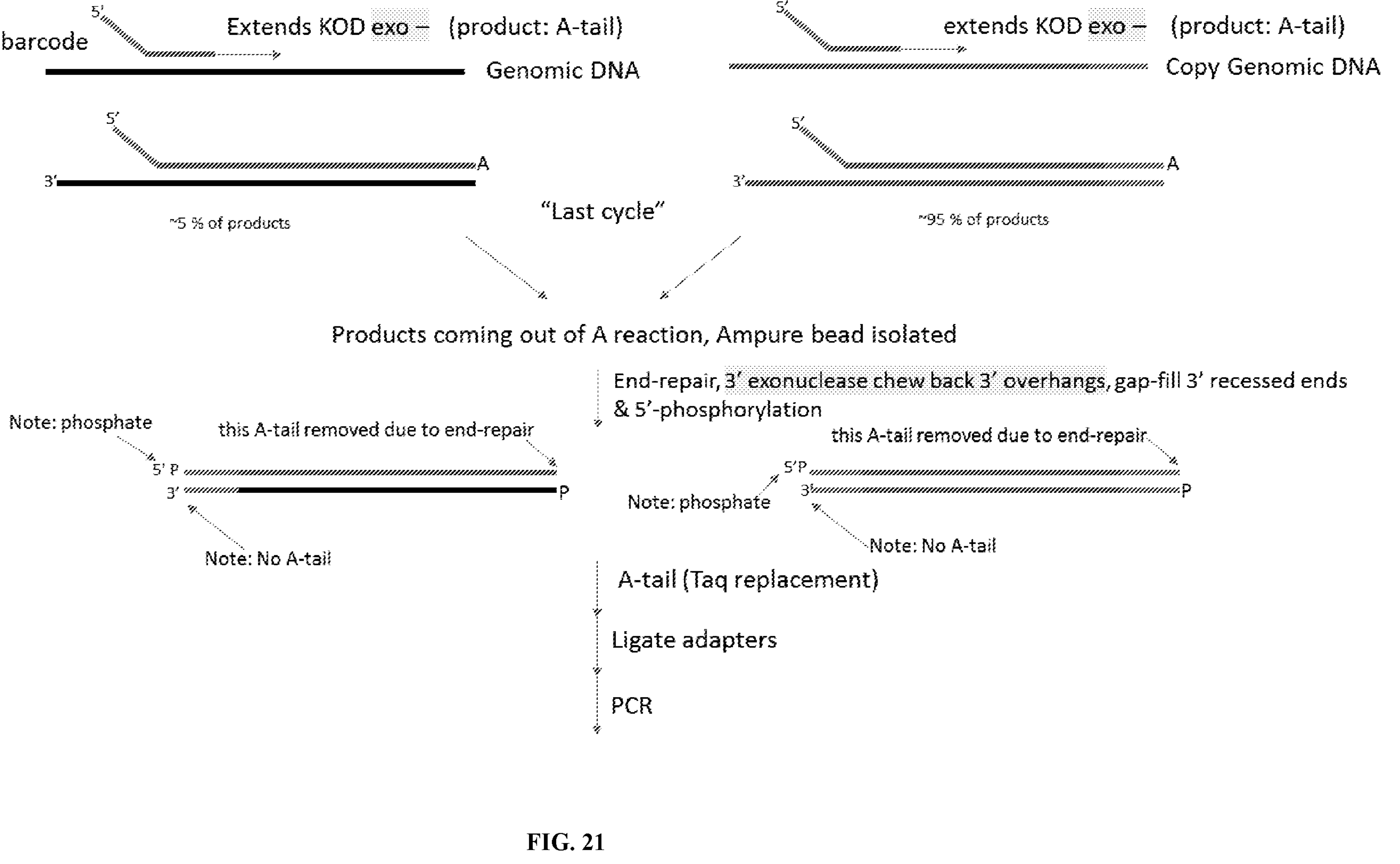
FIG. 21 shows $exo^{-}$ random primed template generation.

A sequencing template is generated using exo$^-$ polymerase and barcoded primers. Such a method is illustrated in FIG. 21. Genomic DNA and copies of genomic DNA are amplified via extension of a barcoded primer by an exo$^-$ polymerase producing A-tailed amplicons which are isolated using Ampure beads. Amplification products are end repaired using 3' exonuclease to remove 3' overhands, gap-filling is used to fill 3' recessed ends, and 5' ends are phosphorylated. Taq polymerase is used to extend A-tails, adapters are ligated and the products are subjected to PCR to create the final template for sequencing.

Example 3: Template Generation Using Exo$^+$ Polymerase

Figure 22:
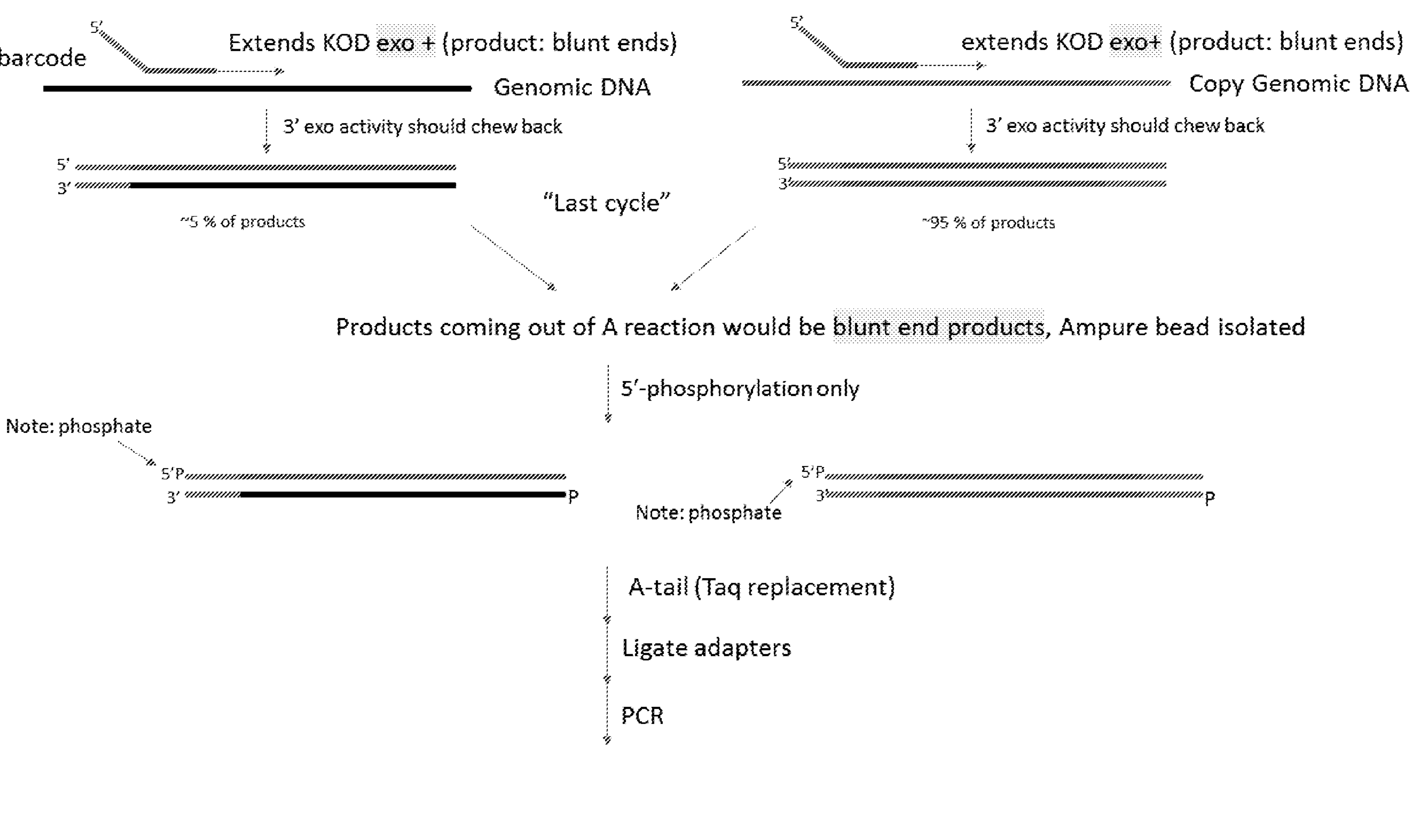
FIG. 22 shows $exo^{+}$ random primed template generation.

A sequencing template is generated using exo$^+$ polymerase and barcoded primers. Such a method is illustrated in FIG. 22. Genomic DNA and copies of genomic DNA are amplified via extension of a barcoded primer by an exo$^+$ polymerase producing blunt ended amplicons which are isolated using Ampure beads. Amplification product 5' ends are phosphorylated. Taq polymerase is used to extend A-tails, adapters are ligated and the products are subjected to PCR to create the final template for sequencing.

Example 4: Template Generation Using Chemical Ligation

A sequencing template is generated by ligating the nucleic acid and the barcode through chemical reactions. Such a method is illustrated in FIG. 23. A nucleic acid having one or more chemical functional groups can react with the chemical groups on the barcode and the chemical reaction can help form a covalent bond that will join the nucleic acid and the barcode. The chemical groups can be at the terminal of the nucleic acid and also at the terminal of the barcode. The chemical groups can be at the 3'-end or 5'-end of one or both strands of the nucleic acid. Examples of the chemical groups that can be used in the chemical ligation scheme include but are not limited to alkyne and azo groups. After the chemical ligation step, the ligated nucleic acid can have barcode at both ends of both strands of the nucleic acid. Tag ligase or ampligase can be used to seal up the nicks on opposite strand. The ligated nucleic acid molecules further undergo PCR to generate multiple copies of final template for sequencing. In some instances, the barcode which has chemical groups may further undergo the activation step that would result in a functional group that reacts with the chemical group on the nucleic acid. As shown on the right side of FIG. 23, the barcode which contains a S—S moiety may undergo an activation step to produce a S—H group which would later react with the acrylamide group on the nucleic acid before forming the ligated nucleic acid.

Example 5: Template Generation Using Tagmentation

Figure 24:
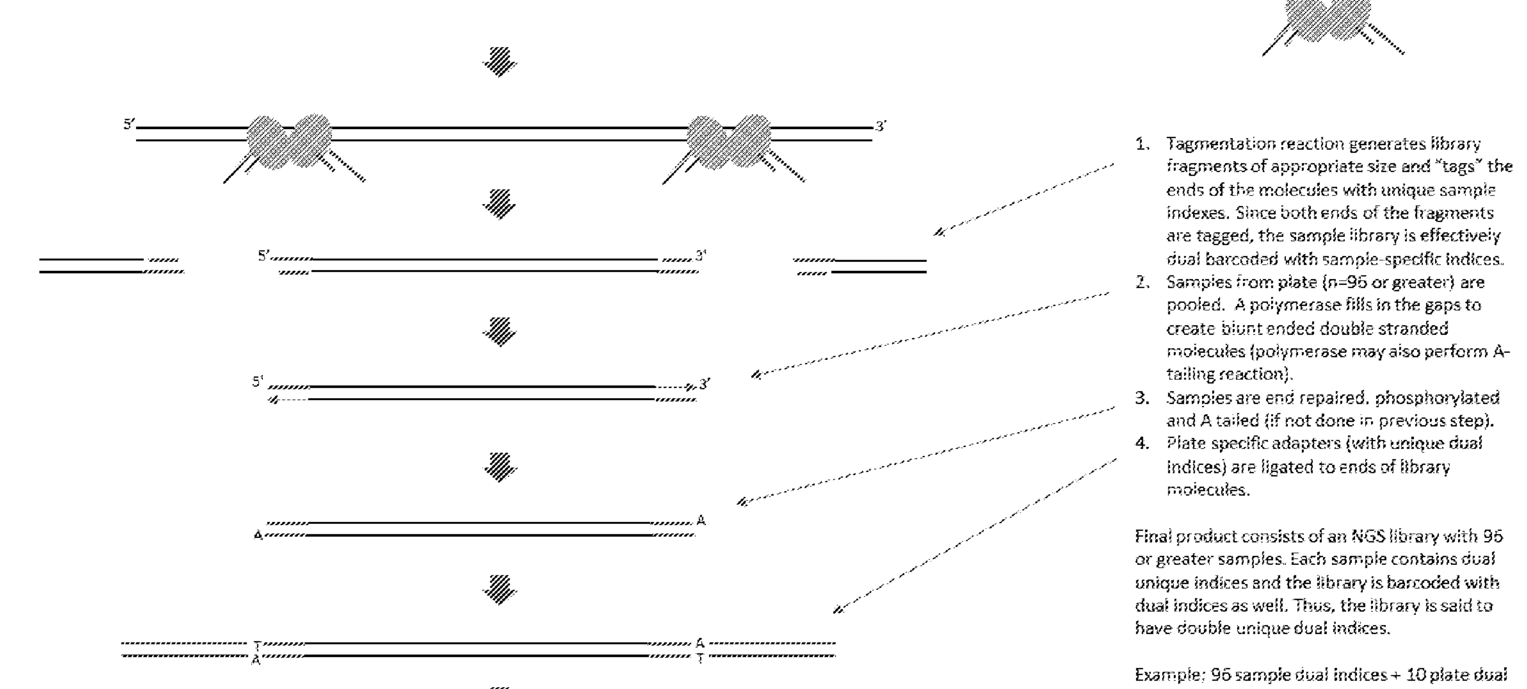
FIG. 24 shows transposase template generation.

A sequencing template is generated from genomic DNA using a transpososome complex with sample specific molecular barcodes. Such a method is illustrated in FIG. 24. Transpososome complexes having sample specific molecular barcodes (unique dial) are used (n=96, 384, 1536, etc). Tagmentation reactions generate library fragments of appropriate size and "tags" the ends of the molecules with unique sample indexes. Since both ends of the fragments are tagged, the sample library is effectively dual barcoded with sample-specific indices. Samples from plate (n=96 or greater) are pooled. A polymerase fills in the gaps to create blunt ended double stranded molecules (polymerase may also perform A-tailing reaction). Samples are end repaired, phosphorylated and A tailed (if not done in previous step). Plate specific adapters (with unique dual indices) are ligated to ends of library molecules. Final product is an NGS library with 96 or greater samples. Each sample contains dual unique indices and the library is barcoded with dual indices as well. Thus, the library is said to have double unique dual indices. For example, a library may have 96 sample dual indices+10 plate dual indices=960 individually barcoded samples.

Figure 25:
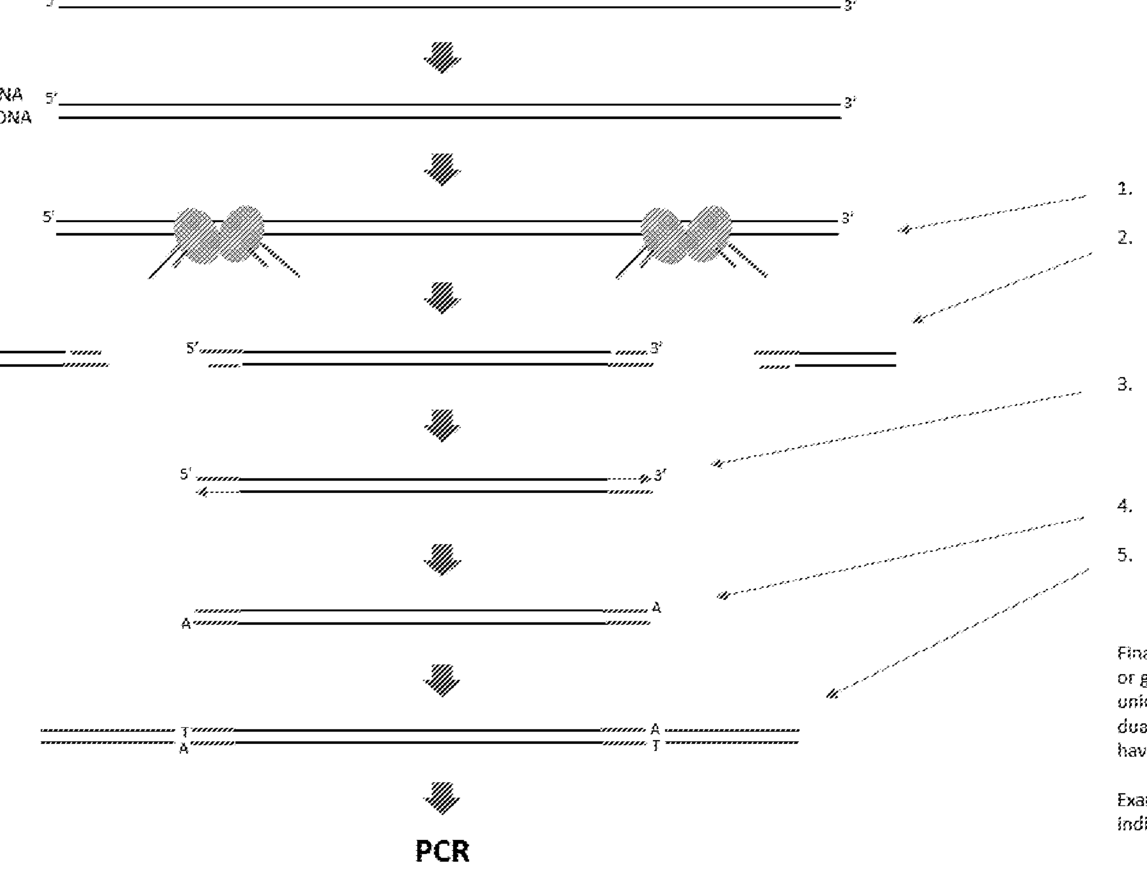
FIG. 25 shows transposase template generation.

In an alternative method illustrated in FIG. 25. A transpososome complex is used with sample specific molecular barcodes (unique dual), n=96, 384, 1536, etc). Tagmentation occurs in double-stranded RNA-DNA hybrid molecules. Tagmentation reaction generates library fragments of appropriate size and "tags" the ends of the molecules with unique sample indexes. Since both ends of the fragments are tagged, the sample library is effectively dual barcoded with sample-specific indices. Samples from plate (n=96 or greater) are pooled. A polymerase fills in the gaps to create blunt ended double stranded molecules (polymerase may also perform A-tailing reaction). Samples are end repaired, phosphorylated and A tailed (if not done in previous step). Plate specific adapters (with unique dual indices) are ligated to ends of library molecules. Final product consists of an NGS library with 96 or greater samples. Each sample contains dual unique indices and the library is barcoded with dual indices as well. Thus, the library is said to have double unique dual indices. For example, a library may have 96 sample dual indices+10 plate dual indices=960 individually barcoded samples.

Example 6: Template Generation Using Tagmentation and Y-Shaped Adapters

Figure 26:
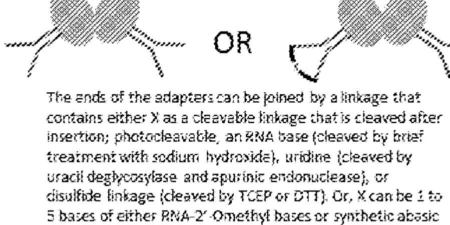
FIG. 26 shows transposase template generation with Y-shaped adapters.

A sequencing template is generated from genomic DNA using a transpososome complex with sample specific molecular barcodes (unique dual), n=96, 384, 1536, etc) and Y-shaped transposon ends. This Example is illustrated in FIG. 26. The ends of the adapters can be joined by a linkage that contains either X as a cleavable linkage that is cleaved after insertion; photocleavable, an RNA base (cleaved by brief treatment with sodium hydroxide), uridine (cleaved by uracil deglycosylase and apurinic endonuclease), or disulfide linkage (cleaved by TCEP or DTT). Or, X can be 1 to 5 bases of either RNA-2'-Omethyl bases or synthetic abasic bases that will inhibit bypass of the polymerase during amplification step in the PCR. Tagmentation reaction generates library fragments of appropriate size and "tags" the ends of the molecules with unique sample indexes. Since both ends of the fragments are tagged, the sample library is effectively dual barcoded with sample-specific indices. Samples from plate (n=96 or greater) are pooled. A polymerase fills in the gaps (but does NOT displace the strand) and a ligase seals the gap. The sample pool is amplified with individually barcoded Illumina P5 and P7 primers. Final product consists of an NGS library with 96 or greater samples. Each sample contains dual unique indices and the library is barcoded with dual indices as well. Thus, the library is said to have double unique dual indices. Example; 96 sample dual indices+10 plate dual indices=960 individually barcoded samples.

Example 7: Template Generation Using Template Switching Method

A sequencing template is generated using a template switching method illustrated in FIG. 27. This method is used on 96 or more DNA samples. Each DNA sample is fragmented (enzymatically or by shearing). DNA is heat denatured. The template is random primed with reverse transcriptase, such as MMLV reverse transcriptase (MMLV can use RNA or ssDNA as template). The random primer carries barcode unique to each sample and a partial Illumina adaptor. MMLV adds a non-templated C nucleotide at each end. Oligo with GGG overhang (included in the reaction) anneals to CCC sequence. Oligo contains barcode unique to sample and partial Illumina adapter. Reverse transcriptase fills in remaining 3' sequence in a process known as template switching. Samples are pooled (96 or greater per plate). PCR is performed with full length Illumina adapter containing primers to generate NGS library with unique dual barcodes.

Example 8: Elimination of Genomic DNA from Library Template

One of the issues with the random primed DUDI seq application is the Genomic DNA carryover. A very small fraction of the molecules in the sample after two rounds of amplification contain the dual barcoded structure. This affects the quantification of the library for loading onto a sequencer, which results in underloading (less data) or overloading (no usable data).

Figure 29:
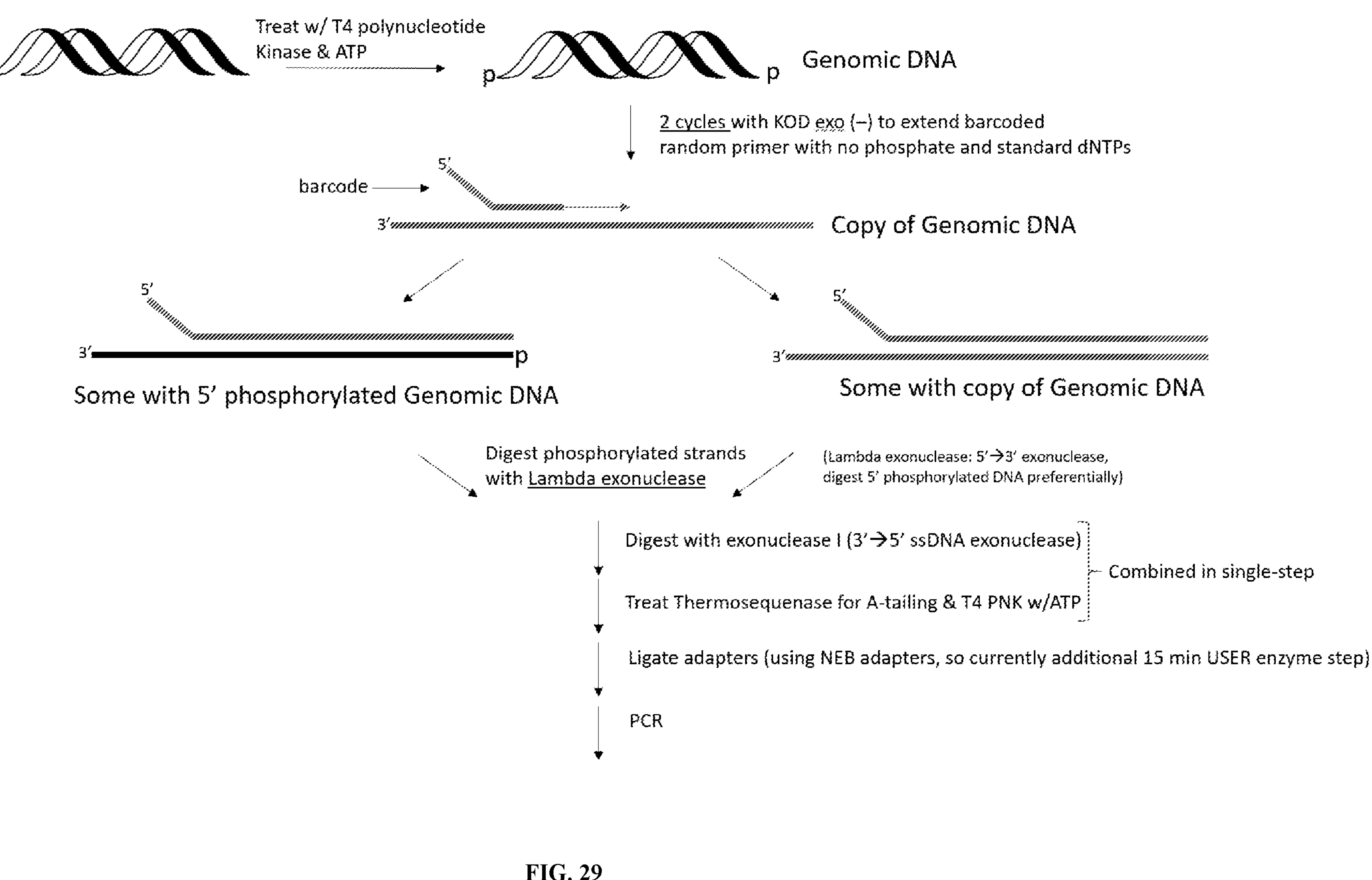
FIG. 29 shows an exemplary workflow for eliminating genomic DNA from the library using T4 polynucleotide kinase and lambda exonuclease.

First the genomic DNA is treated with T4 polynucleotide kinase and ATP to phosphorylate the ends. Then, two cycles of extension with KOD exo(−) is done to extend barcoded random primers with no phosphate and standard dNTPs to create a copy of the genomic DNA. Genomic DNA is eliminated from this product using lambda exonuclease which preferentially digests 5' phosphorylated DNA. Then thermosequenase and T4 polynucleotide kinase are used on the remaining library before ligating the second set of adapters. This approach is illustrated in FIG. 29.

Figure 30:
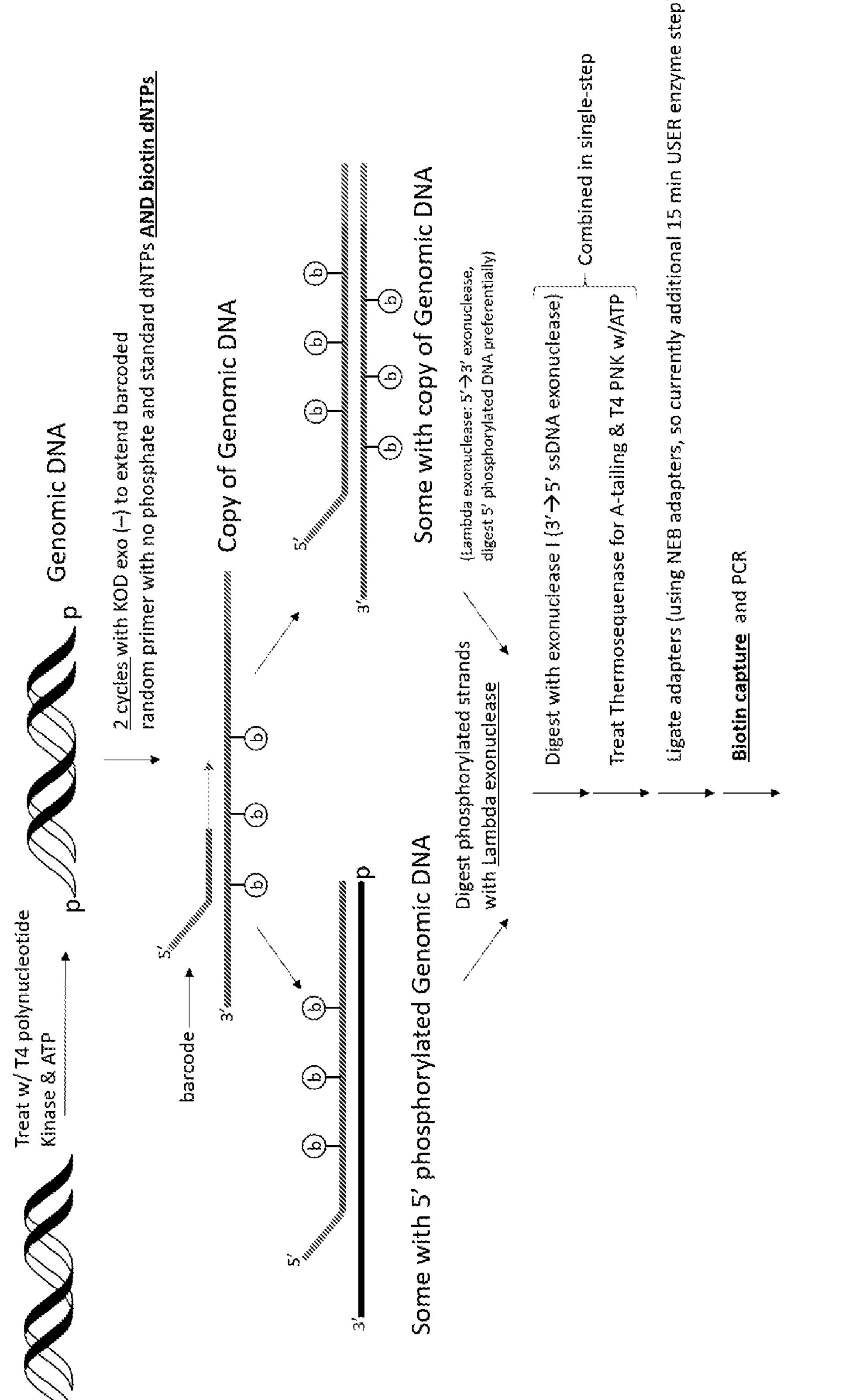
FIG. 30 shows an exemplary workflow for eliminating genomic DNA from the library using T4 polynucleotide kinase, lambda exonuclease, and biotin capture of the library.

An alternate approach is used using biotin-streptavidin to purify the library. In this approach genomic DNA is treated with T4 polynucleotide kinase and two cycles of KOD exo(−) is used to extend barcoded random primer with no phosphate and a mixture of dNTPs and biotin dNTPs. Genomic DNA is eliminated using lambda exonuclease. The remaining library is treated with thermosequenase and T4 polynucleotide kinase before ligating the second set of adapters. Finally the library is captured using streptavidin. This approach is illustrated in FIG. 30.

Figure 31:
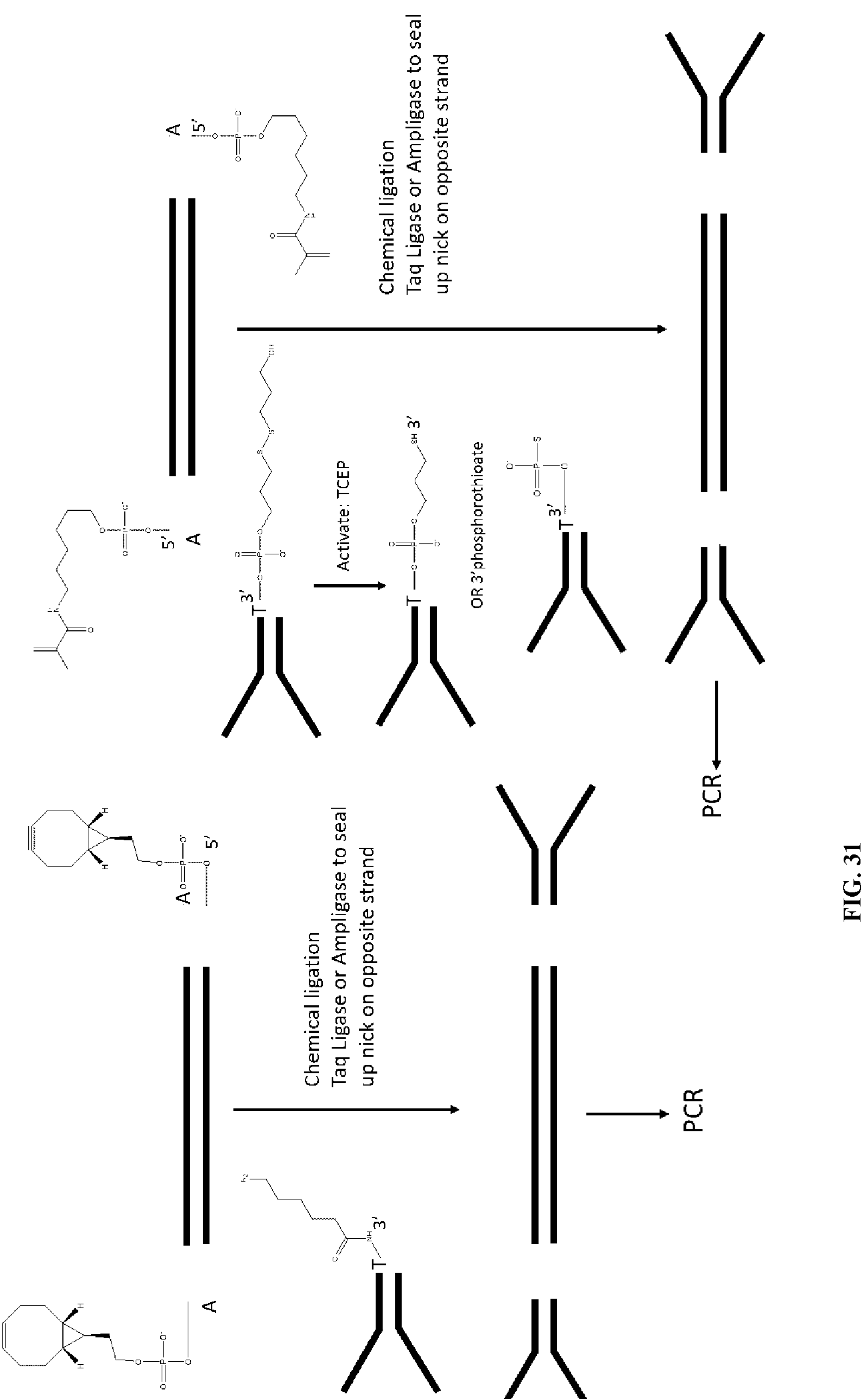
FIG. 31 shows an exemplary workflow using chemical ligation of adaptors.

Another approach utilizes chemical ligation to attach the second set of primers. This approach is combined with one of the previous two workflows, as illustrated in FIG. 31.

Figure 32:
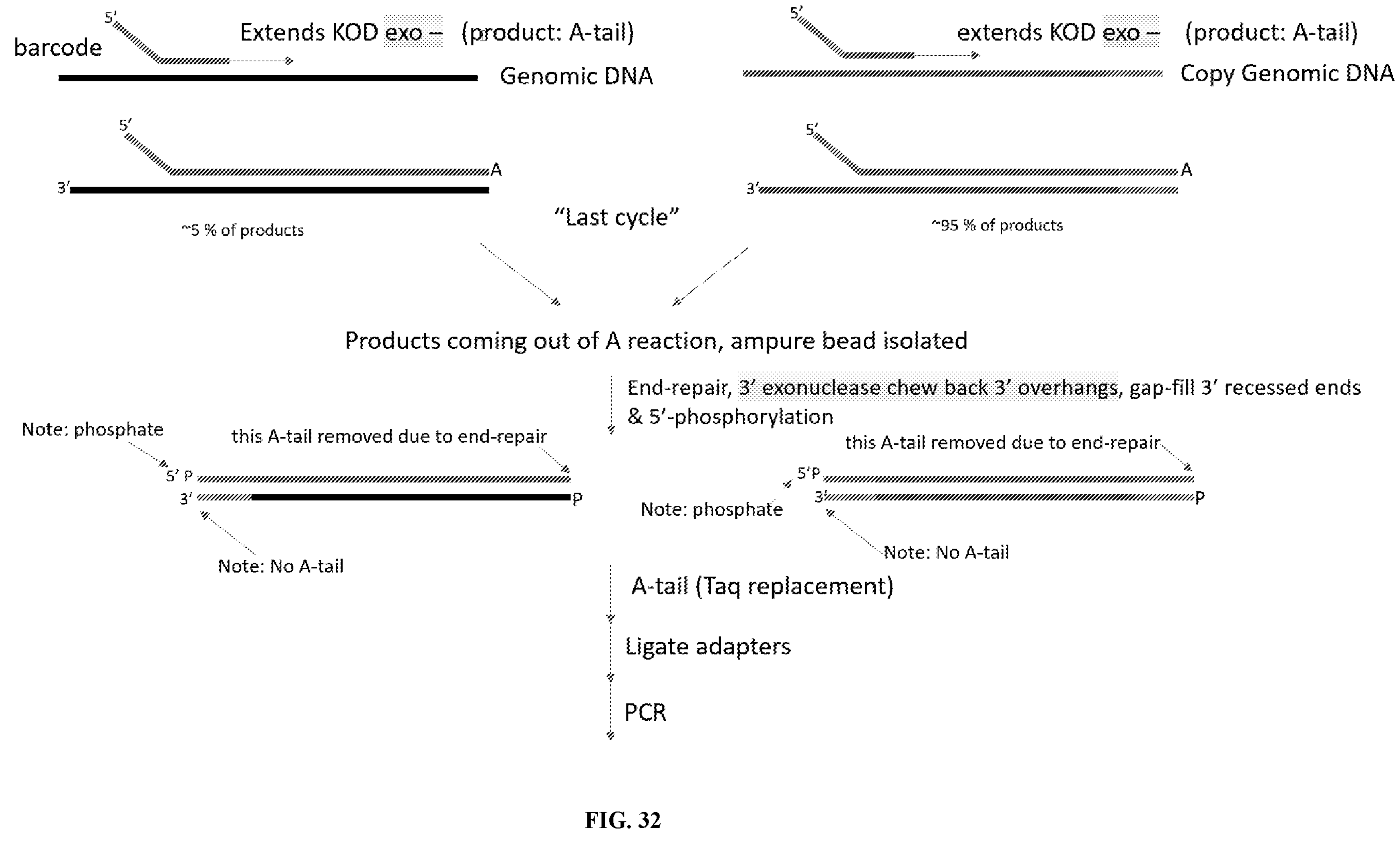
FIG. 32 shows an exemplary workflow using exonuclease created blunt ends.
Figure 33:
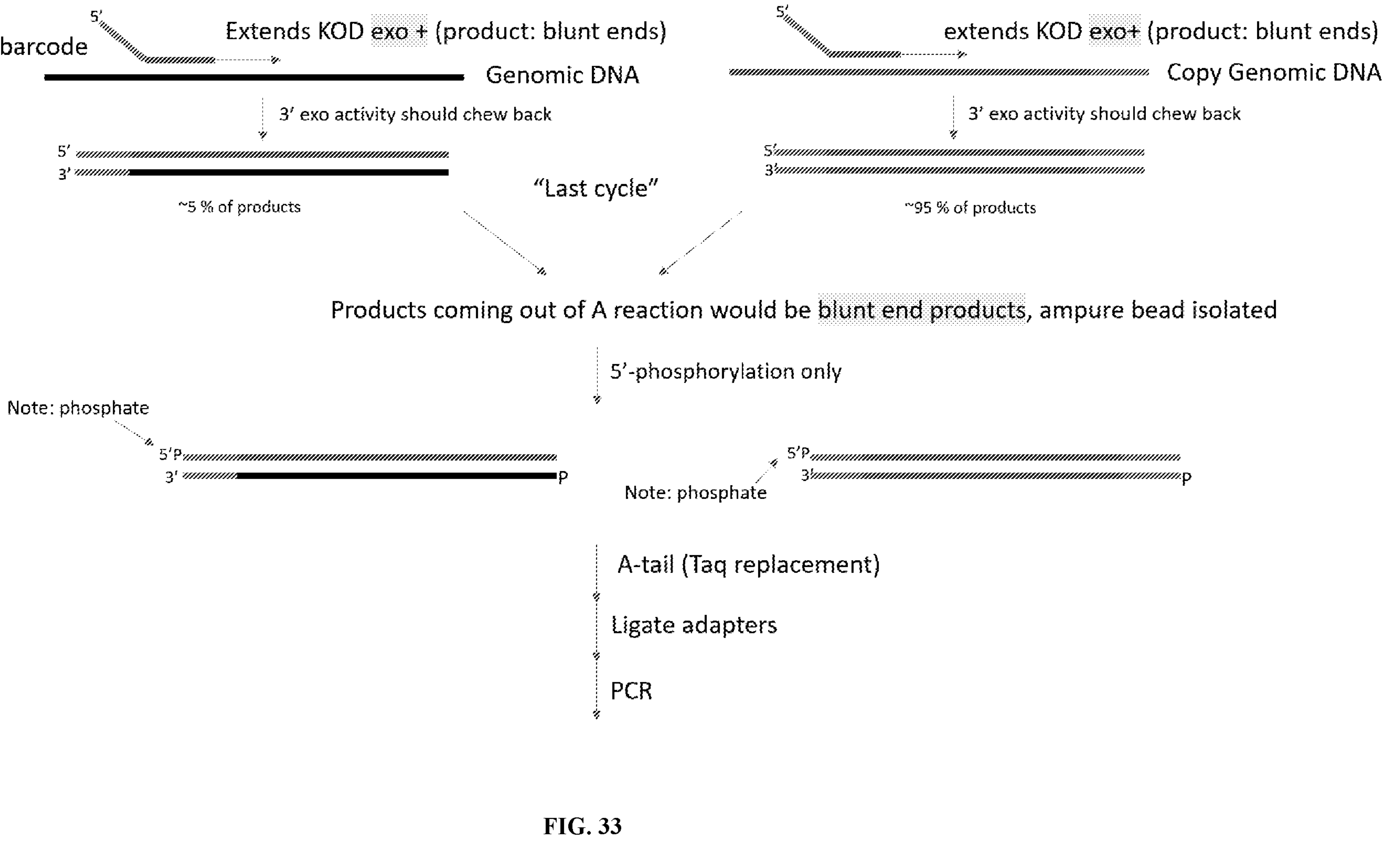
FIG. 33 shows an exemplary workflow using exonuclease to create blunt ends.

In another approach illustrated in FIG. 32 and FIG. 33 the barcoded library is created with KOD exo- and genomic DNA is trimmed using 3' exonuclease which chews back 3' overhangs. The '3 recessed ends are filled and phosphorylated. An A-tail is added before ligating the second set of adapters.

Figure 34:
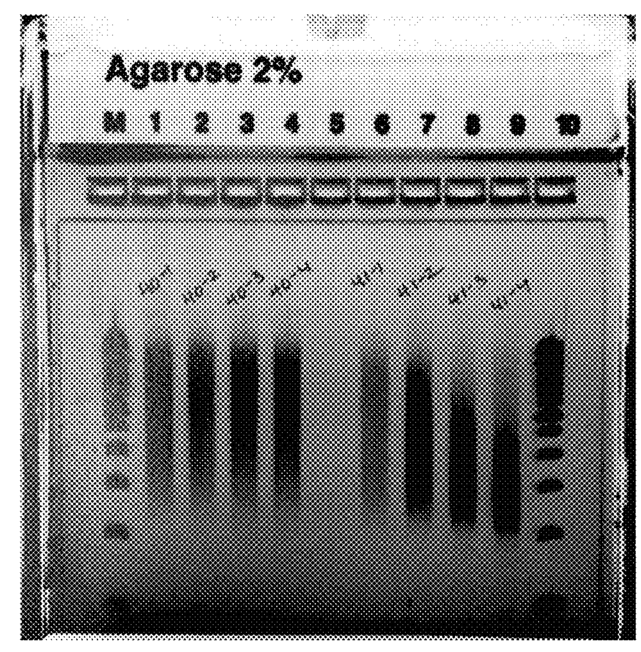
FIG. 34 shows an agarose gel analysis of libraries made with increasing levels of biotin.

The resulting library from biotin purification is shown in FIG. 34 where libraries created with no biotin, a control, 2% biotin, 5% biotin, and 10% biotin were run on a 2% agarose gel. These libraries were sequenced in Nextseq Midoutput run and sequenced well. There was no bunching up of large DNA at the top of the gel, showing that the genomic DNA was eliminated using these approaches.

Figure 35:
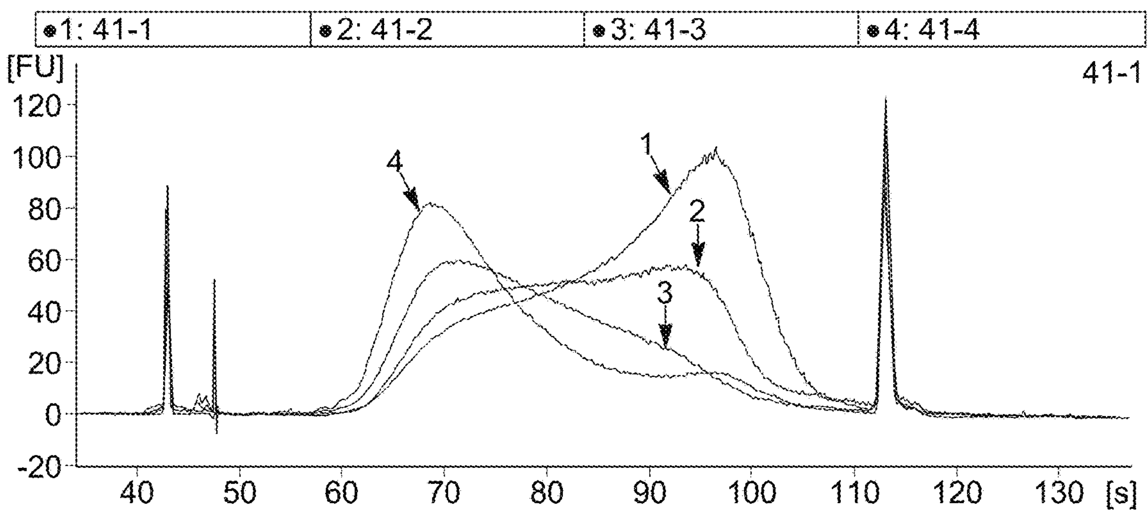
FIG. 35 shows agilent bioanalyzer trace analysis of libraries made with increasing levels of biotin.
Figure 36A:
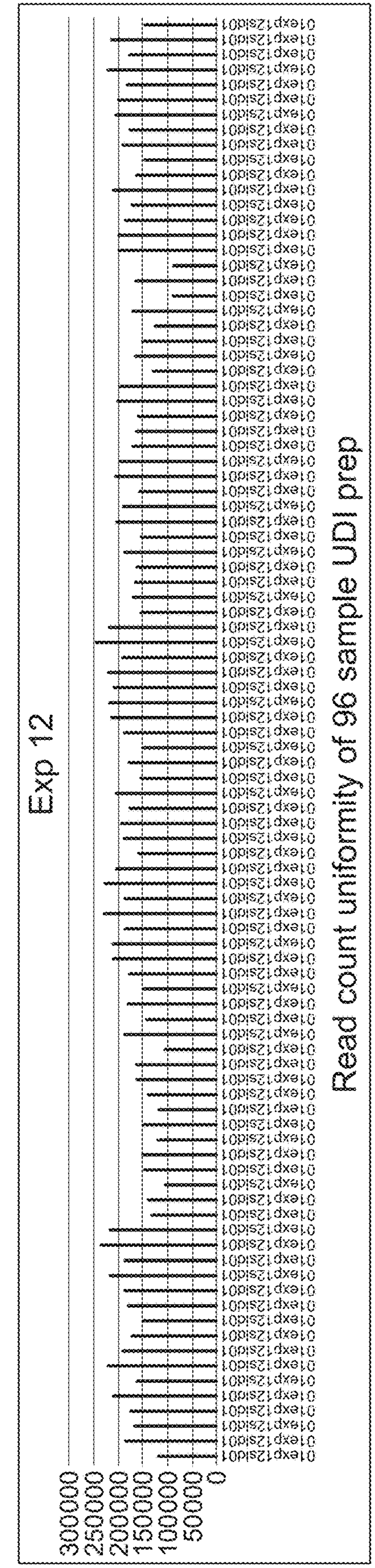
FIGS. 36A-D show read count uniformity (FIG. 36A), alignment scores (FIG. 36B), genomic origin (FIG. 36C), and RSeQC (FIG. 36D) for libraries created from RNA using RT-PCR and barcode addition.
Figure 36B:
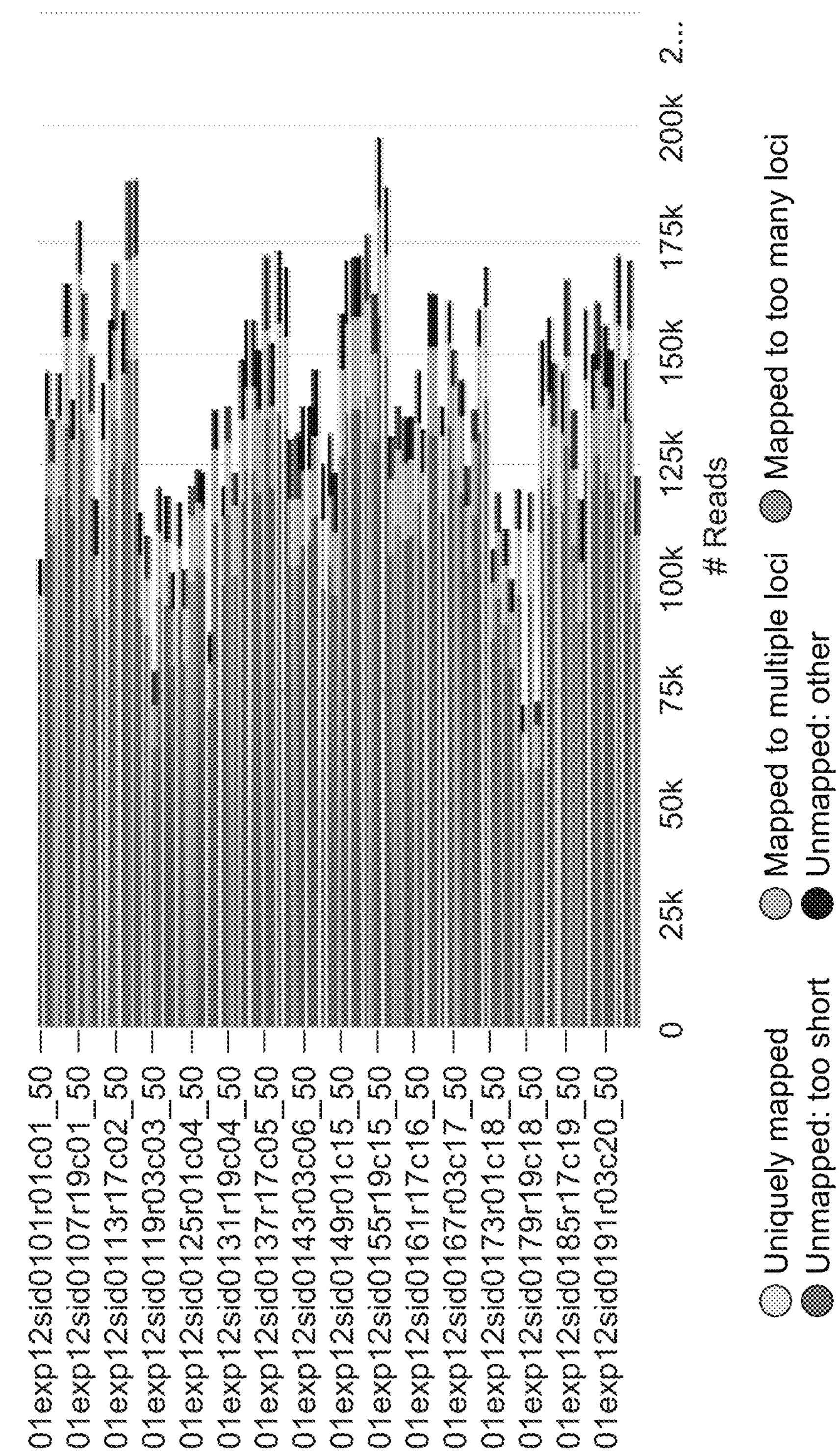
Figure 36C:
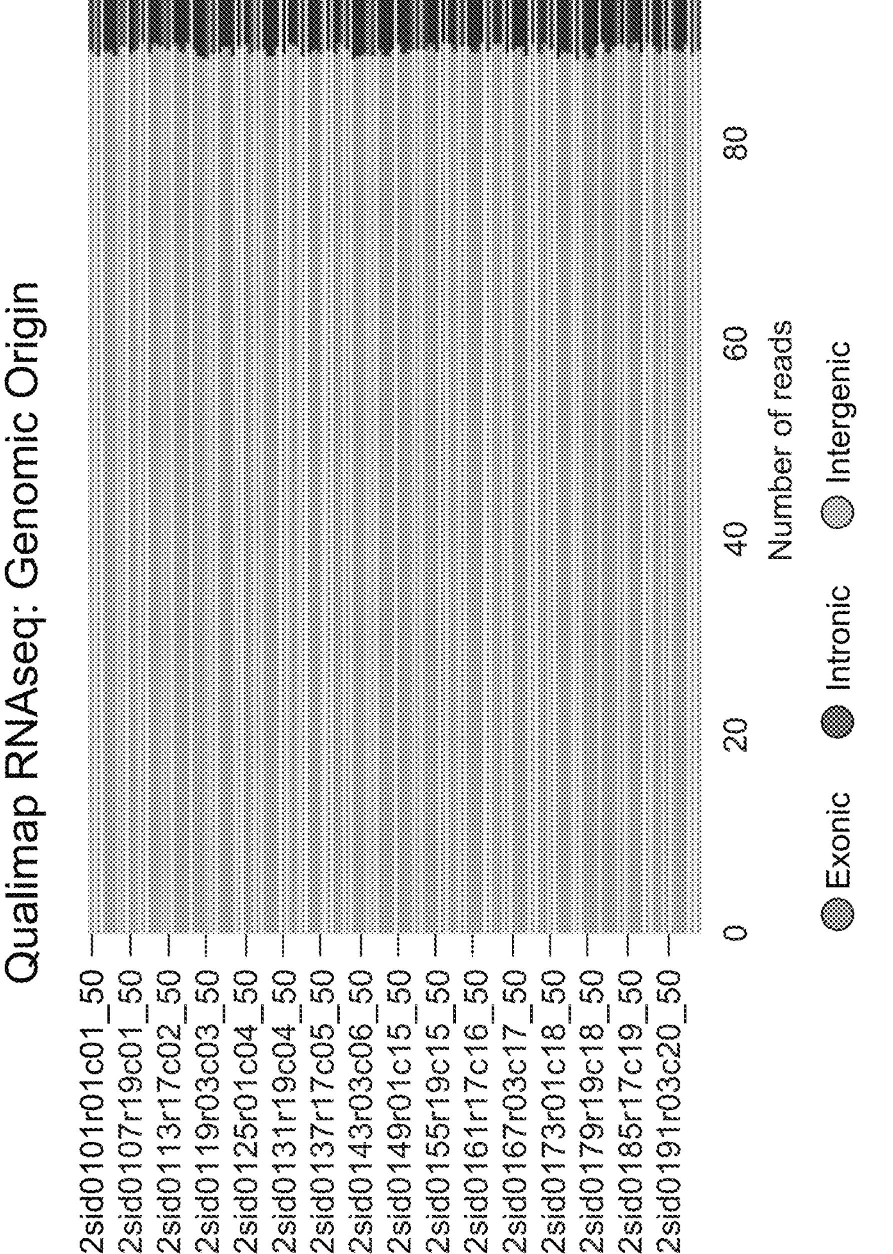
Figure 36D:
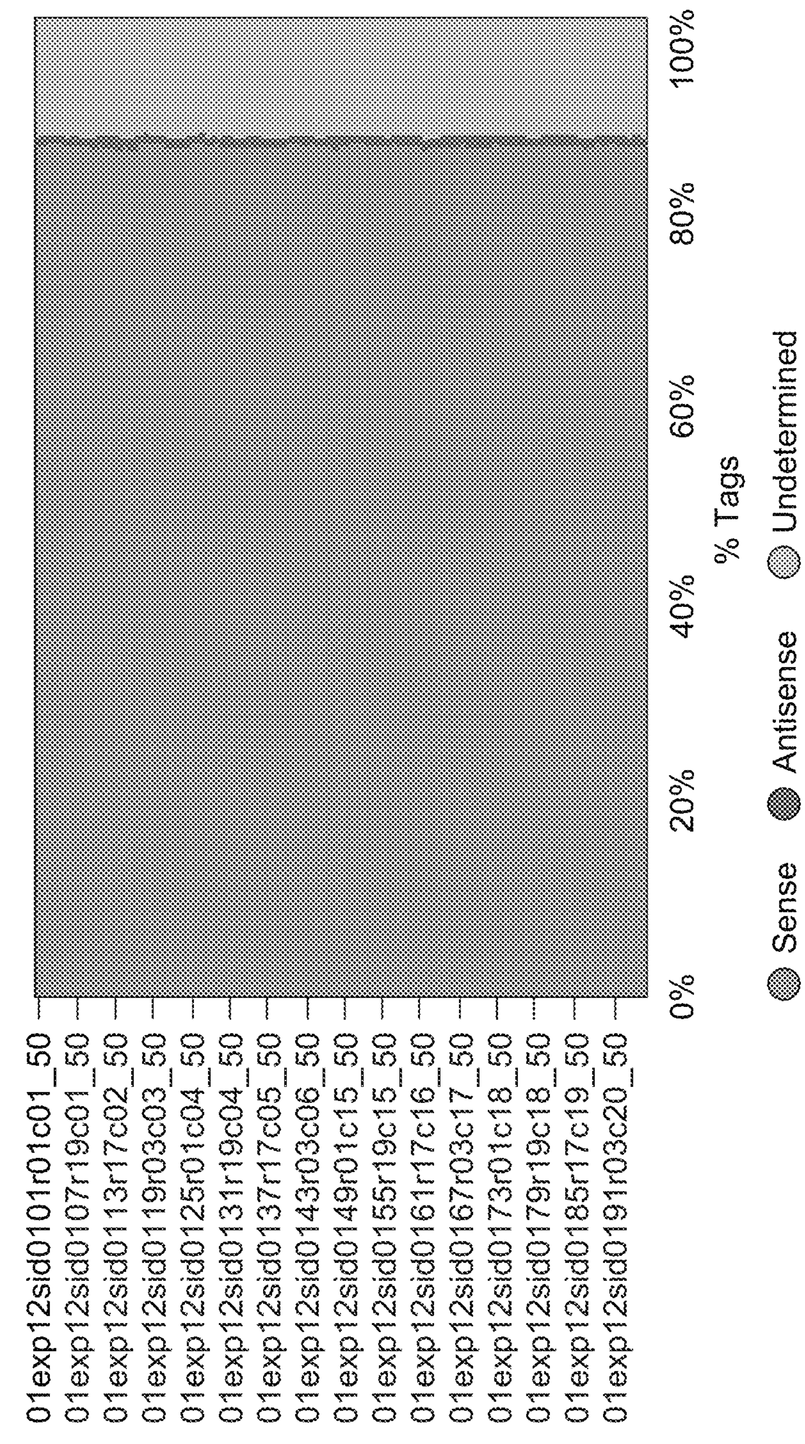

By incorporating biotinylated dNTPs into the initial priming reactions, the dual bar coded molecules were isolated from the genomic DNA background through a streptavidin bead capture. By increasing the amount or ratio of biotin dNTP to native dNTP tuning of the product lengths of the reaction was achieved as shown in the agilent bioanalyzer traces in FIG. 35. The mechanism by which this sizing is thought to be by increased biotin incorporation, biotin molecules on the same template are closer to one another and the proximity means binding to more streptavidin molecules on the beads that are close in proximity. In FIG. 35 trace 1) no biotin, trace 2) 2%, trace 3) 5%, and trace 4) 10%. This technique in some cases eliminates the need for size selection.

Example 9: Double Unique Dual Indexing Library Generation for Sequencing RNA Samples RNA samples were used to make Double Unique Dual Indexing libraries. RNA was reverse transcribed directly from cell lysate to make cDNA. The second barcode was added via polymerization of the DNA construct. Results including read count uniformity, alignment scores, and genomic origin are shown in FIG. 36.

Example 10: Read Count Normalization

Individual libraries need normalization in the multiplex pool because a large disparity in molecules between samples would result in differential read counts per sample. This causes some samples to not get enough sequencing reads, necessitating re-processing. In order to address this issue, post library normalization is used using deactivated CAS9 to target the double stranded barcodes in the library. With bead bound dCAS and guide RNAs specific to the ds target being the limiting reagent equivalent molar ratios of each library or sample are obtained. Addition of biotin or other 5' position modified pyrimidine nucleotides (dC or dT) as an effort to control product size distribution, more incorporation results in smaller products. Further Use of LNAs complementary to the barcode sequences are also used directly after the pooling stage and prior to ligation of the plate adapters to the pool

Example 11: DUDI-Seq-Single Tube Library Preparation

A DUD-seq single tube library preparation with 50 ng DNA input is prepared as follows. First a barcode cycling reaction (A Reaction) is prepared. In put DNA is treated with T4 polynucleotide kinase (PNK) and ATP. To 600 ng of PNK-treated DNA in 12 ul, 2.4 ul of 10×T4 PNK buffer, 1.2 ul of 10 mM ATP, 7.7 ul of nuclease free water, and 1 ul T4 PNK enzyme for a total of 24.3 ul. This is incubated for 1 hour at 37° C. and for 10 minutes at 75° C. The reaction volume and DNA quantity of T4 PNK reaction is accommodated to different numbers of reactions. The reaction volume, in some cases, is reduced to 10 ul and the DNA quantity, in some cases is 100 ng. The A reaction is prepared as follows, 2 ul purified PNK-treated DNA (25 ng/ul, 50 ng input), 3 ul nuclease free water, 2 ul primer A (25 uM, 12 nt randomer) 1 ul 10×KOD buffer, 1 ul dNTP mix (3 mM dNTPs), and 1 ul KOD exo− (2.5 U/ul) for a reaction volume of 10 ul. The reaction is conducted in a thermocycler RT: 1 hour 30 min-2 cycles: 1) 98° C. for 2 minutes; 2) 95° C. for 1 minute, 3) 16° C. for 5 minutes, 4) Slow ramp (0.1° C./sec) to 68° C.; 5) 68° C. for 15 minutes; 6) cycle back to step 2; 7) hold at 4° C. Then 2 ul 150 mM EDTA and 8 ul water is added to inactivate the reaction.

Next the reaction is cleaned up Ampure beads. 20 ul of Ampure beads is added, mixed by pipetting, the incubated at room temperature for 10 minutes to bind DNA. The tube is placed in a magnet and Ampure beads adhere to the tube wall, supernatant is removed and discarded. 150 ul 80% EtOH is added to the beads while the tube is on the magnet It is incubated for 30 sec. then EtOH is removed and discarded. The EtOH wash is repeated and all EtOH is removed after the second wash. The beads are let dry at room temperature for 10 minutes. 28 ul 10 mM Tris-HCl pH 8 is added to the tube off of the magnet and mixed by pipetting and incubated at room temperature for 5 minutes. The tube is put on the magnetic rack then 25 ul is transferred to a fresh tube.

Next the DNA is subjected to end repair, A-tailing, and adapter ligation. The 25 ul DNA is mixed with 1 ul lambda exonuclease (5 U/ul) and 3.5 ul (green) NEBNext Ultra II Buffer (from NEBNext Ultra II DNA Library Prep). The mixture is incubated at 20° C. for 30 minutes, then 75° C. for 10 minutes, then transferred to ice. Then the reaction is mixed with 1 ul Exo I (20 U/ul), 1 ul Thermoseq (diluted to 5 U/ul) and 1 ul T4 PNK (10 U/ul). This is incubated at 35° C. for 30 minutes, then 65° C. for 30 minutes, then 85° C. for 10 minutes, then transferred to ice. To this reaction, 15 ul NEBNext Ultra II Lig Master mix, 0.5 ul NEBNext Ligation Enhancer, 2.5 ul NEBNext Adapter for Illumina (1:10 dilution 1.5 uM) are added for a total volume of 50.5 ul. This is incubated at 20° C. for 15 minutes. Then 1.5 ul of USER Enzyme (necessary for NEB "dumbbell" adapters is added for total volume of 52 ul. This is incubated at 37° C. for 15 minutes.

Then the reaction is cleaned up with Ampure beads. 52 ul of Ampure beads are added and mixed by pipetting. DNA is bound for 10 minutes. The tube is placed on the magnet and the supernatant is removed and discarded. Then the beads are washed twice with 15 ul 80% ethanol. The beads are let to dry for 10 minutes at room temperature and then the tube is removed from the magnet. DNA is eluted with 18 ul 10 mM Tris HCl pH 8. 17 ul of the DNA is used in the next reactions.

Next 8 cycles of PCR are performed. To 17 ul of the PCR product, 4 ul i7 PCR primer (10 uM), 4 ul i5 PCR primer (10 uM), and 25 ul of 2×KAPA PCR Amplification Mix are added for at total volume of 50 ul. PCR is cycled as follows: Input the following parameters into a thermal cycler and perform a PCR: 1. 98° C., 2 min initial hold: 8 cycles: 2. 98° C., 20 sec; 3. 60° C., 30 sec; 4. 72° C., 30 sec (return to step 2); Final step: 72° C., 2 min; 4° C., hold.

The PCR product is cleaned up using the Ampure beads as above. DNA is eluted in 30 ul 10 mM Tris HCl pH 8.0 for the final NGS library. DNA is quantified using the Qubit dsDNA measurement. 15 ul of the library is loaded on a 2% agarose gel to evaluate and/or run a portion on a Tapestation or Bioanalyzer for assessment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A method of preparing a sequencing library from a first nucleic acid sample among a plurality of nucleic acid samples, the method comprising:

annealing a first oligonucleotide comprising a first sample barcode sequence and a first random sequence to the first nucleic acid sample, wherein the plurality of nucleic acid samples includes a first set of samples and a second set of samples, and the first nucleic acid sample is included in the first set of samples;

extending the first oligonucleotide to obtain a first extension product comprising the first sample barcode sequence, the first random sequence, and a first sample sequence;

annealing a second oligonucleotide comprising the first sample barcode sequence and a second random sequence to the first extension product;

extending the second oligonucleotide to obtain a second extension product comprising the first sample barcode sequence, the second random sequence, and a complement of the first sample sequence, thereby obtaining a first double-stranded extension product comprising the first extension product and the second extension product;

attaching a third oligonucleotide comprising a first plate barcode sequence to the first extension product and a fourth oligonucleotide comprising the first plate barcode sequence to the second extension product;

annealing a fifth oligonucleotide comprising a second sample barcode sequence to a second nucleic acid sample, wherein the second nucleic acid sample is included in the second set of samples;

extending the fifth oligonucleotide to obtain a third extension product comprising the second sample barcode sequence and a second sample sequence;

obtaining a second double-stranded extension product comprising the third extension product and a complement of the second sample sequence; and attaching a sixth oligonucleotide comprising a second plate barcode sequence to the third extension product and a seventh oligonucleotide comprising the second plate barcode sequence to a fourth extension product, wherein the first plate barcode sequence is different than the second plate barcode sequence.

2. The method of claim 1, wherein the first sample barcode sequence is specific to the first nucleic acid sample.

3. The method of claim 1, wherein the first plate barcode sequence is specific to the first set of samples, and the second plate barcode sequence is specific to the second set of samples.

4. The method of claim 1, wherein extending is effected using a strand-displacing polymerase, reverse transcriptase, or both.

5. The method of claim 1, wherein the first random sequence and the second random sequence comprise a GC content appropriate for the first nucleic acid sample.

6. The method of claim 1, wherein the first and second extension products comprise a length of about 100 to about 200 bases.

7. The method of claim 1, further comprising purifying the first double-stranded extension product.

8. The method of claim 1, further comprising performing an end-repair reaction on the first double-stranded extension product.

9. The method of claim 1, further comprising performing a phosphorylation reaction on the first double-stranded extension product.

10. The method of claim 1, further comprising performing a polyadenylation reaction on the first double-stranded extension product.

11. The method of claim 1, wherein the third oligonucleotide further comprises a reverse complement nucleic acid sequence of the first plate barcode sequence that forms a hairpin.

12. The method of claim 1, wherein attaching comprises ligating, chemically conjugating, or both.

13. The method of claim 1, further comprising, after attaching the third oligonucleotide and the fourth oligonucleotide, performing PCR on the first double-stranded extension product.

14. The method of claim 1, further comprising subjecting the first double-stranded extension product or the second double-stranded extension product to sequencing.

15. The method of claim 1, wherein the first nucleic acid sample comprises genomic DNA that has not been fragmented.

16. The method of claim 1, wherein the method further comprises performing at least one phosphorylation reaction on the first nucleic acid sample.

17. The method of claim 16, wherein the at least one phosphorylation reaction is performed prior to annealing the first oligonucleotide to the first nucleic acid sample.

18. The method of claim 16, wherein the at least one phosphorylation reaction is performed subsequent to extending the second oligonucleotide.

19. The method of claim 16, further comprising degrading the first nucleic acid sample with a lambda exonuclease subsequent to extending the second oligonucleotide.

20. The method of claim 1, wherein obtaining the second double-stranded extension product comprises:

annealing a seventh oligonucleotide to the third extension product, wherein the seventh oligonucleotide comprises the second sample barcode sequence extending the seventh oligonucleotide to obtain the fourth extension product, thereby obtaining the second double-stranded extension product.

* * * * *